United States Patent
Scarrow et al.

(10) Patent No.: US 9,642,653 B2
(45) Date of Patent: May 9, 2017

(54) SPINOUS PROCESS FIXATION DEVICE AND SYSTEMS

(71) Applicant: Mercy Medical Research Institute, Springfield, MO (US)

(72) Inventors: Alan Scarrow, Springfield, MO (US); Vinoth Sivapatham, Springfield, MO (US); Martin Reuter, Flemington, MO (US); Rahul Eapen, Monett, MO (US); Keela Davis, Springfield, MO (US)

(73) Assignee: Mercy Medical Research Institute, Springfield, MO (US)

( * ) Notice: Subject to any disclaimer, the term of this patent is extended or adjusted under 35 U.S.C. 154(b) by 431 days.

(21) Appl. No.: 14/024,437

(22) Filed: Sep. 11, 2013

(65) Prior Publication Data
US 2014/0074166 A1     Mar. 13, 2014

Related U.S. Application Data

(60) Provisional application No. 61/699,605, filed on Sep. 11, 2012.

(51) Int. Cl.
*A61B 17/80* (2006.01)
*A61B 17/70* (2006.01)

(52) U.S. Cl.
CPC ...... *A61B 17/7064* (2013.01); *A61B 17/7067* (2013.01); *A61B 17/7068* (2013.01)

(58) Field of Classification Search
CPC ............ A61B 17/7064; A61B 17/1757; A61B 17/1671; A61B 17/7067
(Continued)

(56) References Cited

U.S. PATENT DOCUMENTS 6,626,904 B1 *  9/2003  Jammet ............. A61B 17/7001
                                                    606/266
6,709,435 B2    3/2004  Lin
(Continued)

OTHER PUBLICATIONS

G. Cheh et al., Spine 32, 2253-2257 (2007).
(Continued)

*Primary Examiner* — Mary Hoffman
*Assistant Examiner* — Tara R Carter
(74) *Attorney, Agent, or Firm* — Michael A. Williamson; Polsinelli PC

(57) ABSTRACT

A minimally invasive spinous process fixation system includes dual rigid spinous clamps, each configured to articulate axially along a cylindrical shaft, and together configured to enclose and clamp around the adjacent or superior spinous process by means of opposing and swiveling spherical contact heads with spiked spinous contact faces. The spinous clamps are lockable when desired compression is achieved. A pedicle clamp has right and left clamp bodies for enveloping pre-existing pedicle rods. Each of the right and left clamp bodies includes upper and lower rigid metal plates supporting medial and lateral swivel cups. The upper and lower medial swivel cups engage and clamp about a connecting rod extending from the spinous clamp, and the upper and lower lateral swivel cups engage and clamp about one of the pedicle rods. A channel through the upper and lower metal plates accepts a locking screw to simultaneously tighten and fix the swivel cups in place about the connecting rod and the pedicle rod. A cross-connection between the right and left clamp bodies fixes the right and left clamp bodies together at a selected position.

23 Claims, 16 Drawing Sheets

(58) Field of Classification Search
USPC ............... 606/264–279, 246–249; 623/17.11
See application file for complete search history.

(56) References Cited

U.S. PATENT DOCUMENTS

| | | | |
|---|---|---|---|
| 6,793,656 B1 | 9/2004 | Mathews | |
| 8,016,860 B2 | 9/2011 | Carl et al. | |
| 2007/0233082 A1 | 10/2007 | Chin et al. | |
| 2008/0183218 A1 | 7/2008 | Mueller et al. | |
| 2008/0243186 A1* | 10/2008 | Abdou ............... | A61B 17/7067 606/246 |
| 2012/0226316 A1* | 9/2012 | Dant .................... | A61B 17/705 606/250 |
| 2014/0214083 A1* | 7/2014 | Refai ................. | A61B 17/7055 606/256 |

OTHER PUBLICATIONS

J.M. Cottrell et al., HSS Journal the musculoskeletal journal of Hospital for Special Surgery 2, 12-18 (2006).
K.-S. Cho et al., Journal of Korean Neurosurgical Society 46, 425-430 (2009).
Osteomed®, primaLOK TM Surgical Technique Guide, 2-17 (2012).
Paradigm Spine, coflex-f TM, http://spinerevolution.com/wp-content/uploads/2011/08/coflex_F_detail1.pdf.
Regence Medical Policy Manual, Surgery—Interspinous Distraction Devices (Spacers), Policy No. 155 (2006).

\* cited by examiner

SPINOUS PROCESS FIXATION DEVICE AND SYSTEMS

RELATED APPLICATIONS

This application claims priority to U.S. Provisional Patent Application No. 61/699,605, filed Sep. 11, 2012 and incorporated herein by reference.

BACKGROUND

Spinal fusion surgery is currently the state of the art treatment for a variety of lumbar region pathologies and mal-adaptations that have not responded well to rehabilitative therapies. Conditions necessitating the procedure include degenerative disk disease, severe spinal compression, fractures involving neurological damage, spinal stenosis, tumors and structural instabilities caused by conditions such as scoliosis. Fusion typically involves the use of implantable constructs that facilitate calcification between adjacent levels (segments) of the spine. Pedicle screw and rod constructs are currently widely used to secure adjacent levels by means of metal rods passing through screws embedded on the posterior pedicle regions of the spine. The rigid orientation of these rods allows for alignment and distraction of the spine to a certain degree, diverting the load borne by the fused regions and inhibiting further bone degradation and neurological injury at the fused regions.

Fusion implants have evolved tremendously from early Harrington rod constructs, which utilized thick straight rods and hooks to secure the spine. These presented a high risk of post-operative fracture and tended to apply adverse mechanical stress on adjacent spinal segments. Conventional pedicle screws and rods are highly contoured and machined to adapt to different placement configurations and present the lowest possible profile. They utilize minimally invasive drilling and placement techniques that allow for rapid patient recovery and improved prognosis. However, in spite of these advances, studies indicate that about 43% of lumbar fusion patients develop adjacent segment disease (ASD) requiring fusion of the adjacent levels as well. The immobilization of one set of spinal levels is compensated by increased mobility requirements and mechanical stress on the facet joints of adjacent levels, leading to spine degeneration and stenosis. G. Cheh et al., *Spine* 32, 2253-2257 (2007).

With about 150,000 to 300,000 lumbar fusion procedures being carried out annually, there exists a significant need to secure adjacent spinal levels through revision surgery in the least invasive means possible. J. M. Cottrell et al., *HSS Journal the musculoskeletal journal of Hospital for Special Surgery* 2, 12-18 (2006). Barriers to revision surgery include potential dural tear and root injury related complications as well as the formation of scar tissue following the fusion procedure. The success rate for revision surgery is reported to be 60-80%. K.-S. Cho et al., *Journal of Korean Neurosurgical Society* 46, 425-430 (2009).

Currently, ASD is surgically addressed by fusing adjacent segments using an additional pedicle screw-rod construct (a highly invasive option), or by implanting inter-spinous spacer devices (ISPs). Posterior insertion of ISPs is conducted by placing the ISP between the spinous processes of the segments requiring stabilization. ISPs have been found to benefit elderly patients who have a high risk of complications, osteoporosis or poor general health. A major disadvantage of ISPs is that they are dependent on the distraction of intact and healthy spinous processes. In many cases, lumbar fusion surgery involves a laminectomy or removal of the inferior spinous processes belonging to the fused segments. Thus, these spinous processes are not available to properly seat an ISP. Insertion of conventional ISP devices also involves the removal or disruption of the posterior ligamentous complex (PLC), which is critical to the stability of the spine.

Some static ISP devices do not firmly attach or adhere to the spinous processes and have been implicated in increased osteolysis at the contact points between the implant and bone tissue. For example, the X-Stop® interspinous spacer by Medtronic Inc. features a cylindrical shaft that distracts adjacent spinous processes. The shaft is held in place by compressive forces exerted by an adjustable clamp. Osteolysis at the point of contact between the implant and bone is a concern due to micro-movements of the implant during its effective lifetime. The Vertiflex Superion® is an interspinous spacer similar to the X-Stop, but one which may be implanted into the lumbar spine under local anesthesia on an out-patient basis. The spacer is delivered through a small midline incision and flaps expand from the columnar body of the spacer to secure it between adjacent spinous processes Once implanted, the spacer acts as a support column to open nerve and cord passageways.

Osteomed's PrimaLok™ SP device is a posterior supplemental fixation device intended to temporarily fix the thoracic, lumbar or sacral spine while awaiting bony fusion to take place. The device is intended for use at one level with bone graft material, and is not intended for stand-alone use. Four polyaxial gripping plates are incorporated into the device to grip opposing spinous processes. The polyaxial nature of the plates allows for variation in patient anatomy, unlike the static configurations used in some of the other devices. Due to its temporary nature, implant loosening or migration are possible complications of the PrimaLok SP. Due to its placement with the spinous processes, fracture of the spinous processes is also a possible complication. See Osteomed®, *primaLOK™ Surgical Technique Guide*, 2-17 (2012).

Other conventional implants are intended for rigid fixation with spinous processes. For example, the Medtronic Spire™ System is a spinous process plating system that may supplement Medtronic's CD Horizon® rod and screw system. The Spire System, which may be used as a fusion device, consists of two spiked, titanium compression plates. A compression instrument is used to clamp the two plates together, driving the spikes into bone tissue of adjacent spinous processes. A locking screw achieves rigid fixation of the device. For proper placement and anchoring, the Spire System requires two intact spinous processes. The Aspen® Spinous Process Fixation System (by Lanx®) is a two plate compression system classified as an adjunct to fusion and designed as an alternative to pedicle screws. The Aspen system includes a spiked fixation plate designed to be rigidly affixed to the spinous processes with the use of specialized surgical instruments. A hollow central area serves as a bone graft chamber to facilitate fusion, and also contributes to the implant's ability to share weight load of the spine. The Aspen system is intended for single level use in the thoracic or lumbar spine (T1-S1) for the treatment of degenerative disc disease, spondylolisthesis, spinal trauma or spinal tumor. Implant migration and spinous process fracture are possible complications of the Aspen system. Shah, Mitesh V., *TLIF with Unilateral Pedicle Screws and Aspen™ Spinous Process Fixation System*, Spine Universe Case Study Library, http//www.spineuniverse.com/professional/case-studies.

The Coflex-F® is also a non-pedicle supplemental fixation device, including a u-shaped body for resisting relative motion between adjacent levels, with opposing pairs of plates on both sides. The plate pairs include apertures for two pins, allowing the pairs of plates to be press-fit to opposing spinous processes, with the pins passing through holes that are punched in each of the spinous processes. Safety and efficacy of the device for spinal stabilization without fusion has not been established. The Coflex-F is intended for use with an interbody cage and autogenous bone graft, as an adjunct to fusion at a single level in the lumbar spine (L1-S1). Paradigm Spine, Coflex-F™, http://spinerevolution.com/wp-content/uploads/2011/08/coflex_F_detail1.pdf. As with other of the above-referenced implants, migration and spinous process fracture are possible complications of the Coflex-F device. Regence Medical Policy Manual, *Surgery—Interspinous Distraction Devices (Spacers)*, Policy No. 155 (2006).

U.S. Pat. No. 8,016,860 to Carl et al. seeks to reinforce the spine or correct a spinal deformity with a hood-like element that is positioned over and screwed or bolted onto the spinous process of a first vertebra. A pair of screws connect to the hood at first screw ends and angle outward to connect to pedicle screws that are anchored to opposing pedicles of a third vertebra, at opposing second ends. A cross bar between the two pedicle screws prevents them from creeping laterally. Carl et al. addresses the above-noted problem of spinous process fracture by suggesting that a cavity be created within the spinous process and filled, with a reinforcing material in order to strengthen and support the bone prior to attaching the Carl et al. device.

U.S. Pat. No. 6,793,656 to Matthews also makes use of a cross-member. Matthews discloses a temporary, suprafacial spinal fixation device including pedicle screws with bilateral fixation plates engaged thereover. A pair of linking members is secured between the pedicle screws to laterally connect the plates. The plates are secured to the pedicle screws and the linking members to the plates via top-loaded nuts.

U.S. Pat. No. 6,709,435 to Lin discloses a three-hook device for fixing the spinal column. A first hook is inserted into the spinal canal of a spinal segment, while two length-adjustable hooks engage the spinal projection of the segment. A pair of rods are inserted into apertures on either side of the hook device, so that multiple vertebrae may be fixed by attaching additional three-hook devices to the rods, to engage other vertebrae.

U.S. Patent Application Publication No. 2007/0233082 by Chin describes a pivoting clamp that engages and locks the spinous processes of adjacent vertebrae. Long bolts may be used to anchor the device transversely through a spinous process. U.S. Patent Application Publication No. 2008/0183218 by Mueller is similar to the Chin device, being a clamp with protrusions for engaging and frictionally securing the spinous processes of adjacent vertebrae. However, Mueller does not require boring through a spinous process.

SUMMARY

Given the drawbacks of ISP devices, there exists a need for a device and method for stabilizing adjacent segments that is minimally invasive, that does not require removal or modification of existing implants, that can safely bear mechanical loads and compressive forces imposed by the upper torso, that can be extracted through minimal intervention, that is not prone to migration (as described above with respect to conventional devices) and that does not require attachment to intact inferior spinous segments. The device must also be able to work with an existing fusion system (i.e., a pedicle screw-rod system). The fusion device disclosed herein addresses these needs by docking/attaching to existing pedicle screw-rod systems and making use of a clamping mechanism to the laminae-spinous junction of the superior spinous process.

In an embodiment, a spinous process fixation system for attaching with existing pedicle rods includes a spinous clamp having opposing spinous swivel heads mounted with left and right spinous clamp arms, for clamping a spinous process of a patient's spine therebetween. A left socket is proximate the left clamp arm, and a right socket is proximate the right clamp arm. A barrel base is configured with one of the left and right clamp arms, and a shaft configured with the other of the left and right clamp arms and sized to mate with the barrel base to secure the left and right clamp arms together. Left and right connecting rods each have a ball head at an anterior rod end and are configured for fitting with the respective left or right socket via the ball head. A pedicle clamp assembly of the spinous process fixation system includes a left clamp body and a right clamp body, each having a medial clamp for clamping the respective left or right connecting rod and a lateral clamp for clamping a left or right pedicle rod of a pre-placed pedicle rod and screw construct. The medial and lateral clamps each include opposing upper and lower swivel heads.

In an embodiment, a spinous process fixation system for attaching with existing pedicle rods includes a spinous clamp portion having opposing swivel heads mounted at anterior ends of opposing left and right clamp arms. The left and right clamp arms extend from posterior left and right bases, and each of the left and right bases forms a ball-and-socket-joint posterior to the left and right clamp arms. A left connecting rod extending from the left ball-and-socket joint in a direction opposite the left arm. A right connecting rod extending from the right ball-and-socket joint in a direction opposite the right arm. The left and right bases join via a cylindrical shaft and channel connection that facilitates fixation of the left and right bases with a customized distance and angle therebetween. A pedicle clamp assembly connects at an anterior end with the spinous clamp portion via the connecting rods, and with a pre-implanted pedicle clamp and rod assembly at a posterior end. The pedicle clamp assembly has a left side and a right side, each of the left and right sides comprising a medial connecting rod clamp, for attaching to one of the left and right connecting rods, and a lateral pedicle rod clamp, for clamping to a pedicle rod of the pre-implanted pedicle clamp and rod assembly.

In an embodiment, a minimally invasive spinous process fixation system that achieves rigid fixation of an adjacent or superior spinous process in case of a laminectomy includes dual rigid metal spinous clamps, each configured to articulate axially along a cylindrical shaft, and together configured to enclose and clamp inferiorly around the adjacent or superior spinous process by means of opposing and swiveling spherical contact heads with penetrating spikes on spinous contact faces thereof, the spinous clamps being lockable when desired compression is achieved. A pedicle clamp has right and left clamp bodies for enveloping existing pedicle rods between two consecutive pedicle screws. Each of the right and left clamp bodies includes upper and lower rigid metal plates supporting medial and lateral swivel cups with outer swivel heads and inner wings. The opposing upper and lower medial swivel cups are configured to engage and clamp about a connecting rod extending from the spinous clamp, and the opposing upper and lower lateral swivel heads are configured to engage and clamp about one of the existing pedicle rods. A channel or aperture through the upper and lower metal plates, accepts a locking screw to simultaneously tighten and fix the swivel cups in place about the connecting rod and the pedicle rod. A cross-connection between the right and left clamp bodies fixes the right and left clamp bodies together at a selected position.

DETAILED DESCRIPTION

It should be noted that as used herein, directions and positions (e.g., left, right, anterior, posterior, up, down, medial and lateral), refer to relative position of components of the spinal fixation device when the device is assembled with a human spine, a model or ASTM test blocks. It will also be appreciated that although certain features are described only with respect to the left, right, top or bottom of the device or a component part, location of such features may be changed so long as complementary features are located opposite one another (for example, an acceptor described below as being on the left side, for fitting an extension of the right side, may instead be positioned on the right, so long as the complementary extension is then positioned on the left. Likewise, a socket described as being on a bottom half of the device may be positioned on the top half, so long as a plug meant to fit the socket is then positioned on the bottom half of the device).

Figure 1:
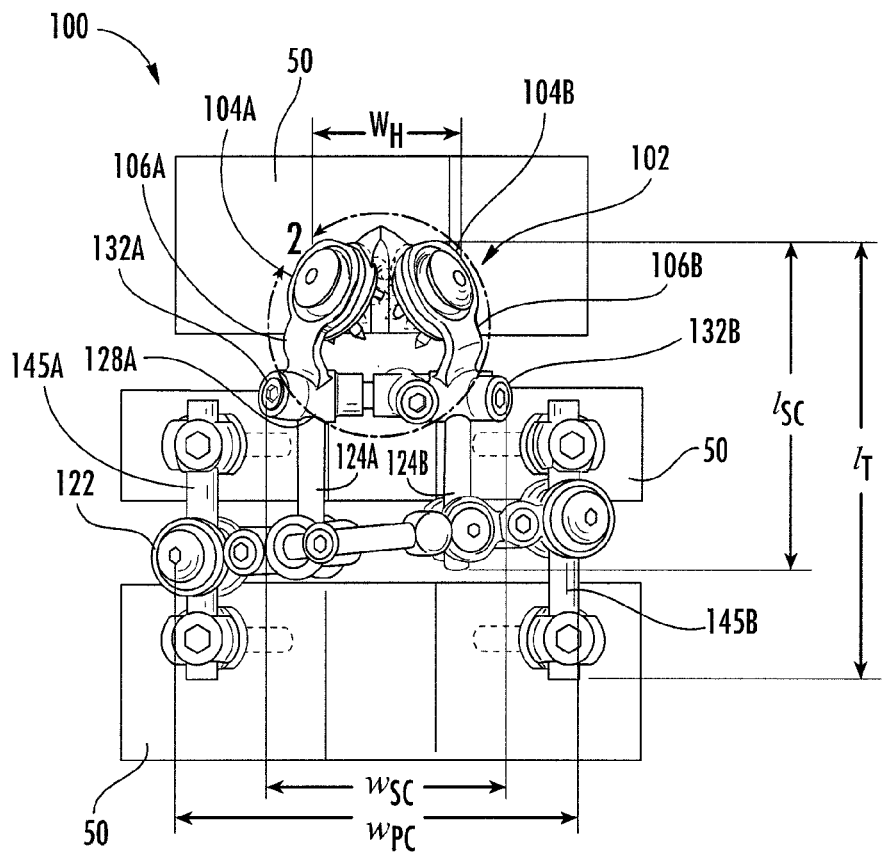
FIG. 1 is a schematic top view of a spinal fixation device including a spinous clamp and a pedicle clamp system and being mounted on ASTM mounting blocks, according to one embodiment.
Figure 2:
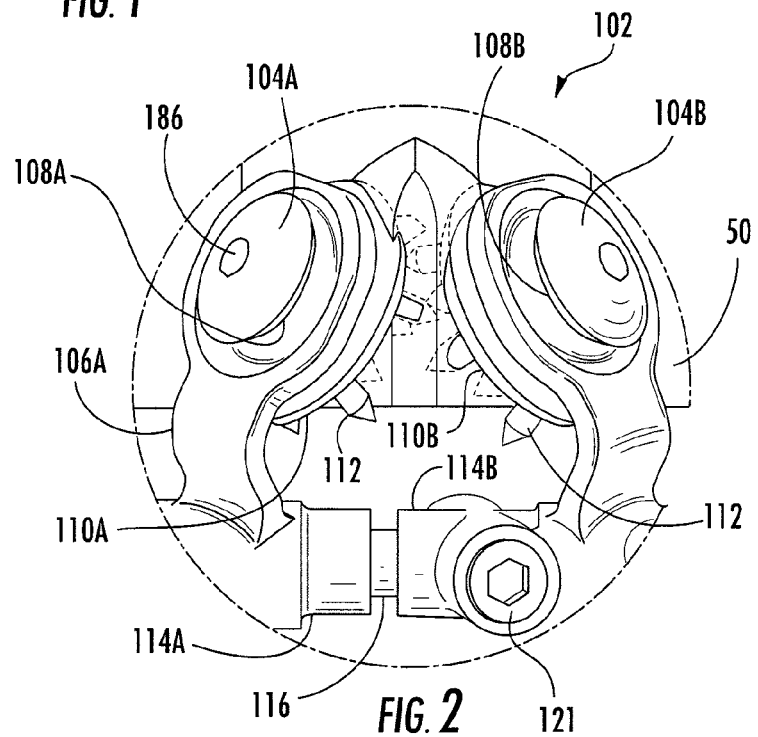
FIG. 2 is an enlarged view of area "2" of FIG. 1, showing a spinous clamp of the spinal fixation device.
Figure 3:
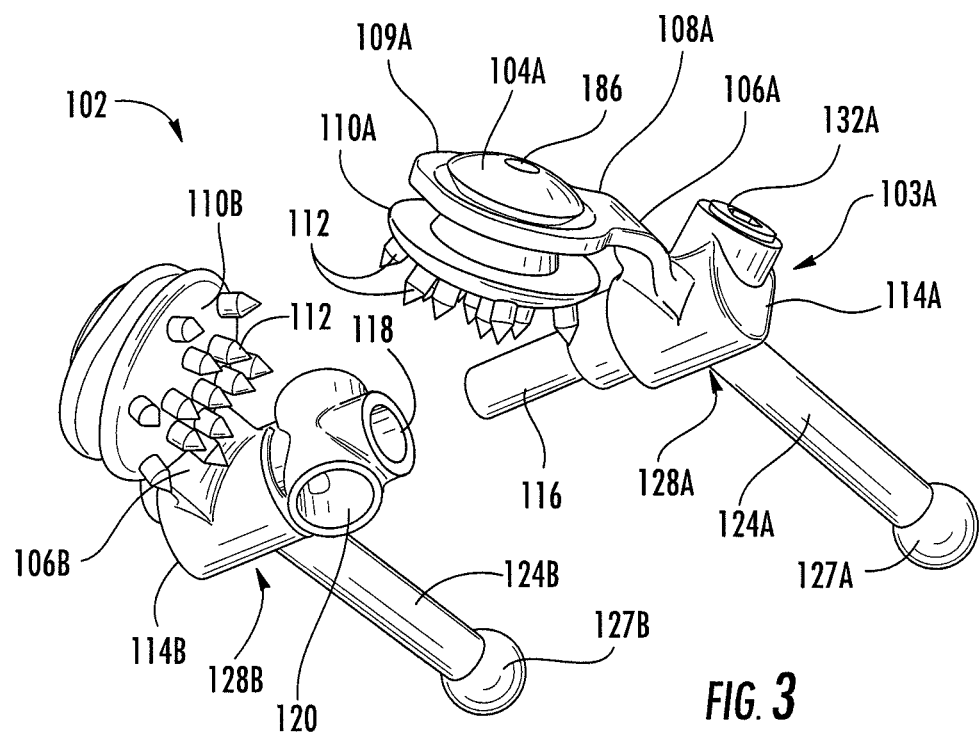
FIG. 3 is a bottom perspective view of the spinous clamp of FIGS. 1 and 2, mounted with a pair of connecting rods having ball ends.
Figure 4:
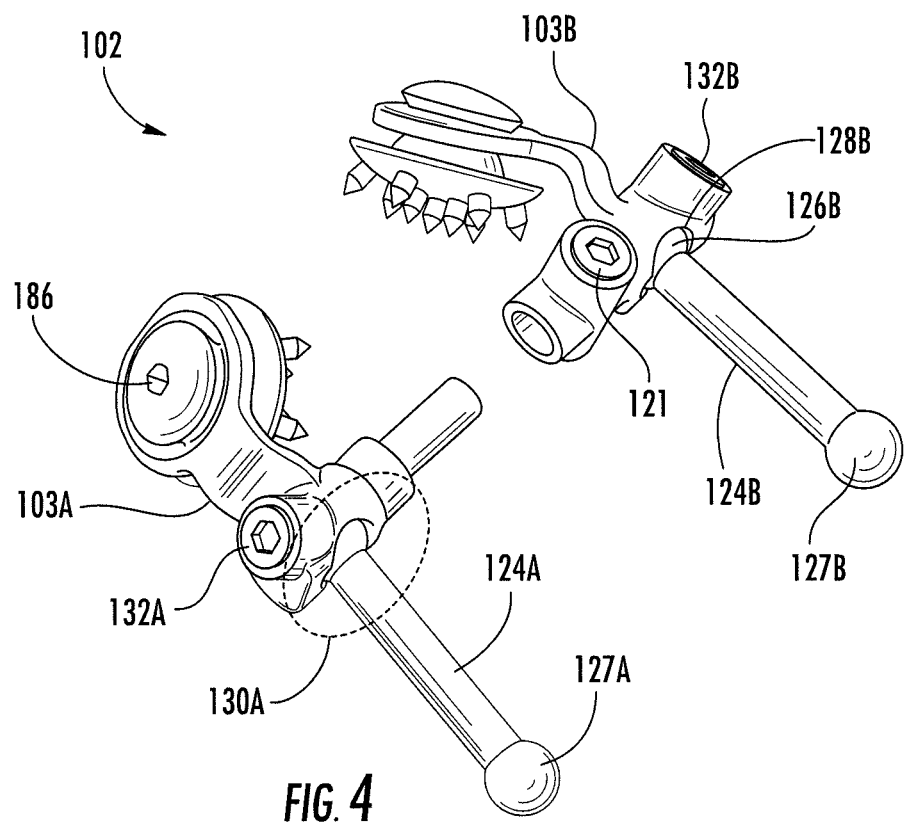
FIG. 4 is a top, perspective view of the spinous clamp of FIG. 3.
Figure 5:
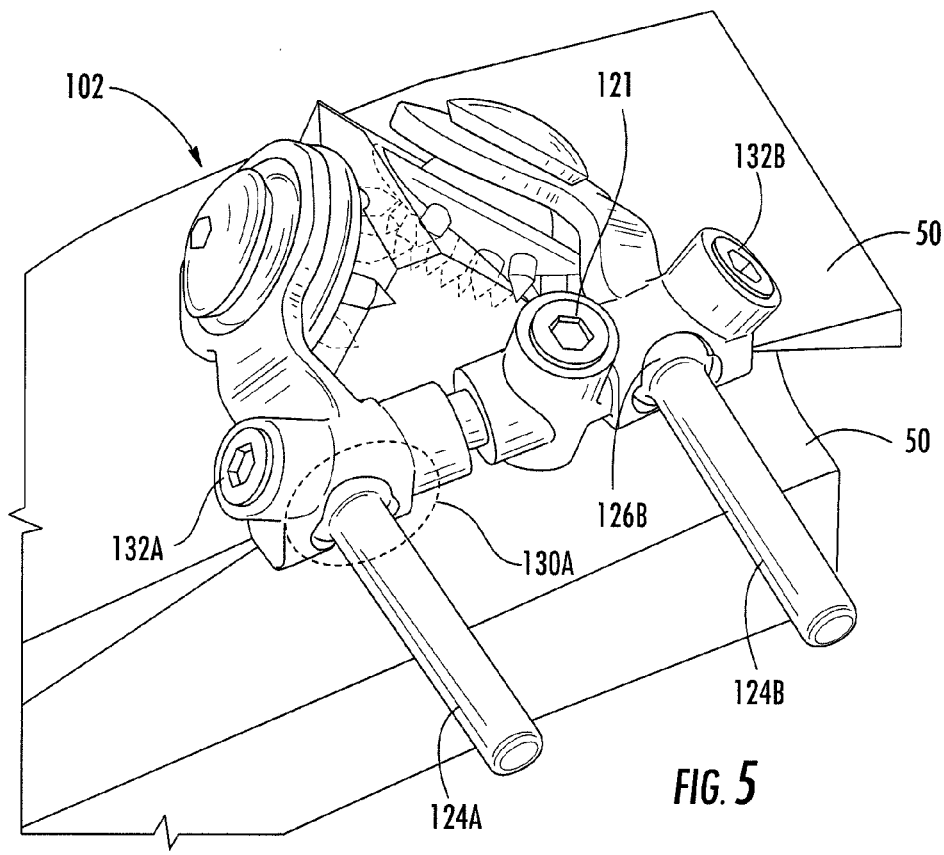
FIG. 5 is a top perspective view of the spinous clamp of FIGS. 1-4, mounted on an ASTM block.

FIG. 1 shows a spinal fixation device 100 mounted with model ASTM blocks 50. Device 100 includes a spinous clamp section 102 having opposing clamp heads 104 (left head 104A and right head 104B) configured with a pair of curved clamp arms 106 (left arm 106A and right arm 106B). FIG. 2 is an enlargement of area D of FIG. 1, showing additional details of spinous clamp section 102. FIG. 3 is a bottom view of spinous clamp section 102, separated into left and right halves 103A and 103B. FIG. 4 is a top perspective view of FIG. 3. FIG. 5 shows left and right clamp halves 103A and 103B joined together and mounted with ASTM blocks 50. FIGS. 1-5 are best viewed together with the following description.

Left and right clamp heads 104A and 104B swivel and rock within respective left and right terminal apertures 108A and 108B of left and right arms 106A and 106B. In one aspect, apertures 108 are beveled or tapered from a front arm surface 109 inward, allowing clamp heads 104 a range of swiveling motion within apertures 108, such that fit between a patient's spinous process an opposing face 110 of each clamp head 104 (also referred to herein as clamp faces or clamping faces 110) may be optimized according to the patient's spinal anatomy, and such that surface area of contact between clamping faces 110 and a patient's laminaspinous junction may be optimized (increased) as well. For example, clamping faces 110 lend a spinous process clamping area of about 479 mm$^2$ to clamp section 102. Clamping faces 110 include radial spikes 112 for gripping or biting into the spinous process, to secure clamp section 102 in place. Radial spikes 112 may provide better anchoring or grip than a perpendicular spike geometry. Firm attachment of clamp section 102 to the spinous process may prevent osteolysis at the point of implant to bone contact.

Opposite heads 104, left and right clamp arms 106A and 106B terminate in respective left and right barrel-like bases 114A and 114B (hereafter, also referred to as barrel bases 114) that are approximately normal to arms 106. Bases 114 connect with one another, thereby joining left and right spinous clamp halves 103A and 103B, via a cylindrical shaft 116. Shaft 116 may run posterior and under the adjacent level spinous process, when clamp section 102 is placed with a patient's spine (i.e., clamping faces 110 are placed about the adjacent level spinous process). In one aspect, shaft 116 is fixed within or formed as an extension of barrel base 114 of one clamp half. For example, FIG. 4 shows shaft 116 as an extension of left barrel base 114A. In this aspect, shaft 116 is sized to fit within a central channel 118 of right barrel base 114B with enough play that left and right clamp halves 103A and 103B may be rotated clockwise or counterclockwise with respect to each other, with shaft 116 rotating within right barrel base 114A and/or right barrel base 114A rotating about shaft 116. Clockwise and counterclockwise rotation of clamp halves 103A and 103B allows a surgeon to adapt fit of spinous clamp section 102 to varying patient anatomy. It will be appreciated that shaft 116 may alternately be fixed with or formed as an extension of right barrel base 114B, and left barrel base 114A may form central channel 118.

An aperture 120 (FIG. 3), formed within or through the barrel base 114 having central channel 118, accepts a set screw 121. Set screw 121 is approximately normal to central channel 118 when placed within aperture 120. As illustrated in FIG. 4, right barrel base 114 includes central channel 118; however, it will again be appreciated that this and other features of clamp halves 103A and 103B may be reversed, so long as mating features are placed opposite one another (e.g., shaft 116 placed opposite central channel 118 with aperture 120 and set screw 121). Set screw 121 may be easily accessed from above during surgery, and tightened to lock left and right clamp halves 103A and 103B in place once a desired clamp section 102 orientation is achieved.

Spinous clamp section 102 connects with a pedicle clamp assembly 122 (see, for example, FIGS. 6 and 7), via a pair of connecting rods 124. Connecting rods 124 may have a diameter of about 4.5 mm. In one aspect, left and right connecting rods 124A and 104B terminate in respective left and right anterior or proximal ends 126A and 126B (proximal to clamp heads 104), which fit with respective left and right sockets 128A and 128B of barrel bases 114A and 114B, forming left and right ball and socket joints 130A and 130B. Ball ends 126 may be press-fitted with sockets 128 (see also FIGS. 4 and 5), such that connecting rods 124 may swivel within sockets 128 to allow for flexibility in connecting with pedicle clamp assembly 122, and to allow for customization of pedicle clamp assembly 122.

Ball and socket cross connectors allow for flexibility in connecting to pedicle clamps in different planes and angles of orientation from spinous clamps. For example, rods 124 may be moved inward, outward, up, down and/or vertically to connect to a pedicle clamp assembly that must be made narrower, wider raised, lowered or uneven in order to conform and connect with a preexisting pedicle rod and screw construct (i.e., with pre-existing pedicle rods 145). Once desired placement of rods 124 with respect to barrel bases 114 is achieved, set screws 132 (FIGS. 4 and 5) may be tightened to lock ball ends 126 into sockets 128. Locking ball and socket joints 130 into place adds stability to spinal fixation system 100 and may prevent metal wear at joints 130. Distal ball ends 127 (at ends of connecting rods 124 that are distal to clamp heads 104) may aid in preventing connecting rods 124 from slipping through clamps of pedicle clamp assembly 122.

As shown in FIG. 1, when assembled, system 100 has a spinal process clamp length $l_{SC}$ (from the top or anteriormost portion of clamp section 102 (on an anteroposterior axis) to the bottom or posterior end of connecting rods 124), a total, piggybacked system length $l_T$ (from the top or anterior-most portion of clamp section 102 to the posterior end of existing pedicle rod 145), a clamp head width $w_H$ (from outer left head 104A to outer right head 104B), a spinous process clamp section 102 width $w_{SC}$ (from outermost edge of left barrel base 114A to outermost edge of right barrel base 114B) and a pedicle clamp width $w_{PC}$ (the distance between centers/dimples 186 of lateral pedicle clamps 146A). In the aspect illustrated in FIG. 4, $l_{SC}$ is 58.14 mm, $l_T$ is 78.78 mm, $w_H$ is 27.21 mm, $w_{SC}$ is 43.32 mm and $w_{PC}$ is 75.46 mm. However, it will be appreciated that all of these dimensions may vary as a function of connecting rod 124 length, position of pedicle clamp assembly 122 on connecting rods 124, angles at which connecting rods 124 join with ball-and-socket joints 130, height and curvature of pedicle clamp assembly 122 and other adjustments described herein below.

Figure 6:
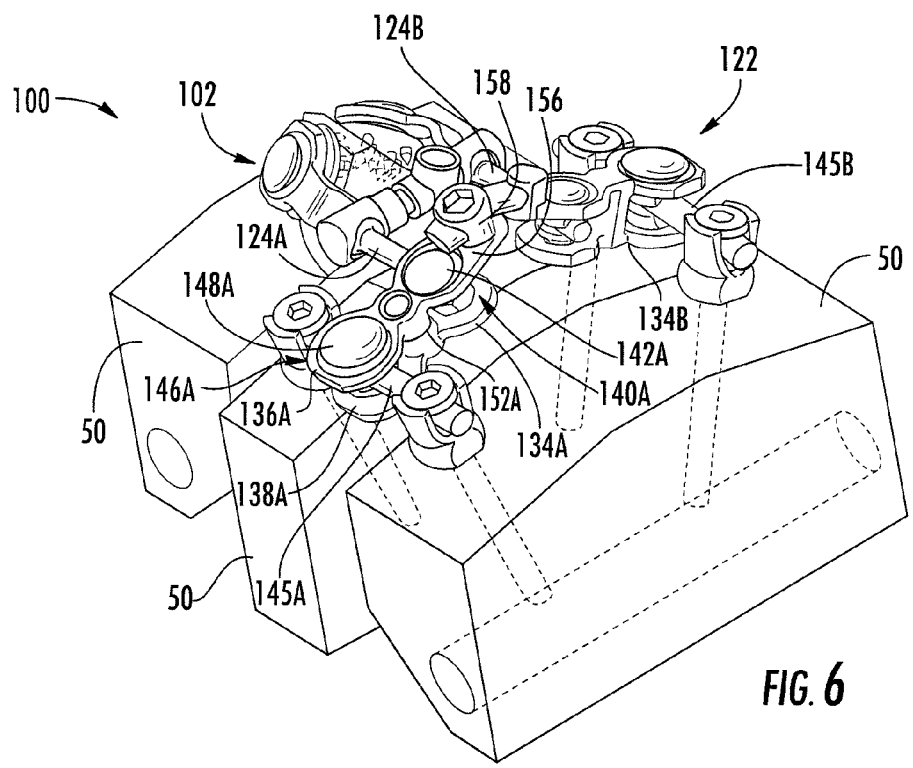
FIG. 6 is a top perspective view of the spinal fixation device of FIG. 1, showing additional detail of a pedicle clamp system, according to an embodiment.
Figure 7:
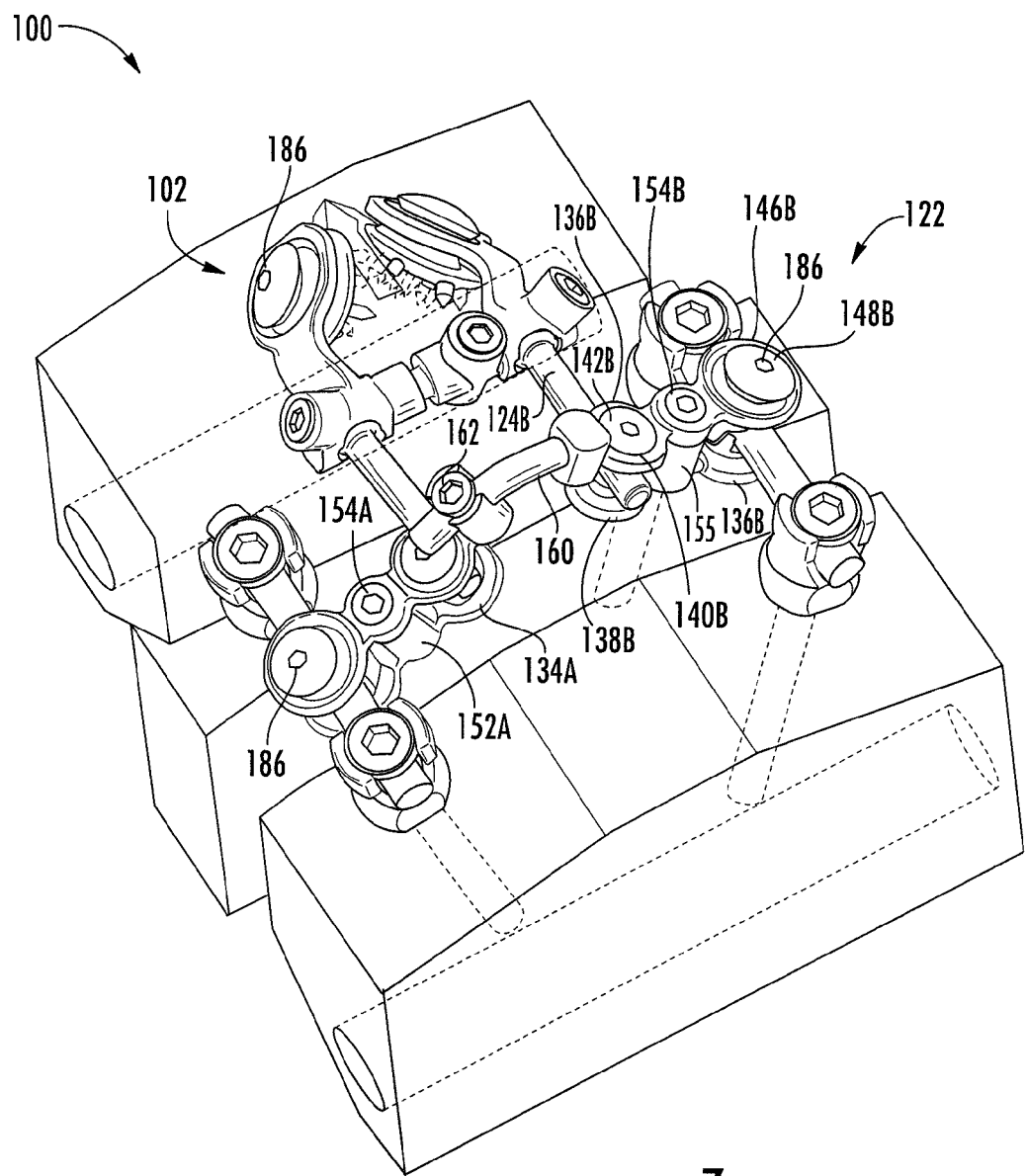
FIG. 7 is a top perspective view of a spinal fixation device similar to that of FIGS. 1 and 6, showing additional locking screws, a slot attachment for joining halves of a pedicle clamp assembly, and other additional features, according to an embodiment.
Figure 8:
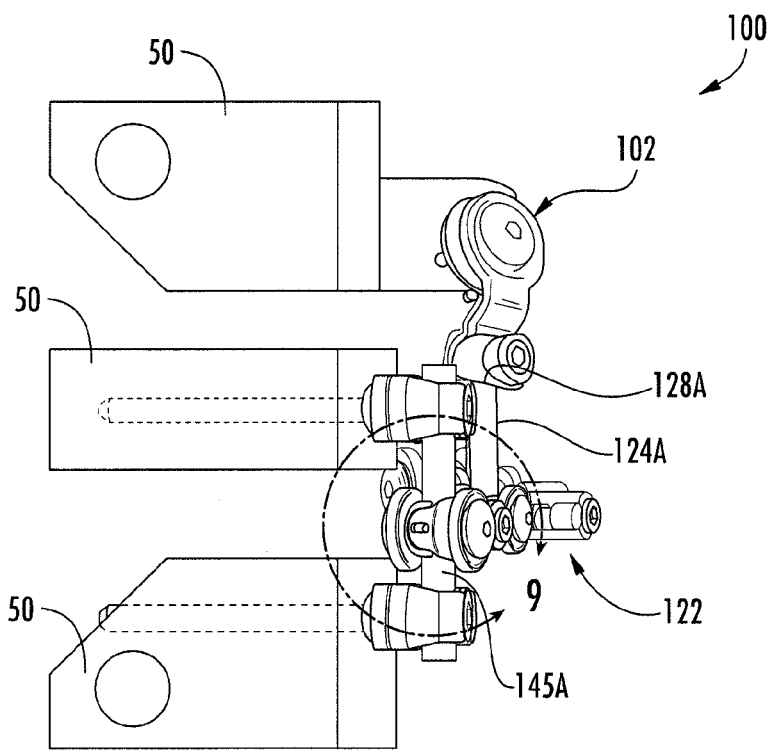
FIG. 8 is a side view of the spinal fixation device of FIG. 1.
Figure 9:
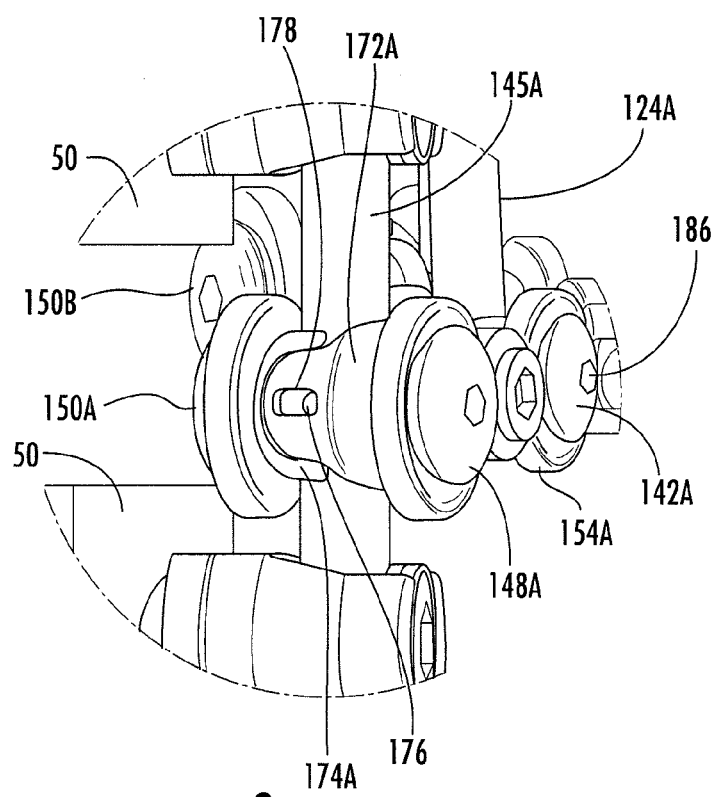
FIG. 9 is an enlarged view of area "9" of FIG. 8.
Figure 13:
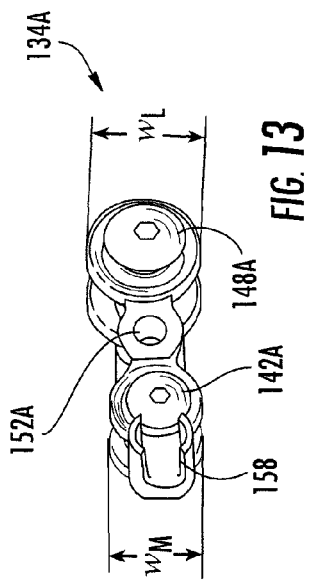
FIG. 13 is a top view of the left pedicle clamp of FIG. 11.

Turning now to FIGS. 6 and 7, connecting rods 124 join spinous clamp section 102 with pedicle clamp assembly 122. Pedicle clamp assembly 122 includes a left clamp body 134A and a right clamp body 134B. Each clamp body 134 includes upper and lower clamp halves or plates 136 and 138. A first or medial clamp 140A of left clamp body 134A clamps left connecting rod 124A of left clamp half 103A (for example, at or proximate a distal or posterior end of rod 124A). Left medial clamp 140A for example includes upper and lower heads 142A and 144A (FIG. 11) that may swivel, rotate or rock within respective upper and lower beveled or angled medial apertures 145A and 147A of left clamp body 134A (see FIGS. 11, 13 and description below). A left second or lateral clamp 146A includes upper and lower clamp heads 148A and 150A (FIG. 9) that grip a pedicle rod 145A (i.e., a previously implanted rod) therebetween. As with medial clamp 140A, upper and lower heads 148A and 150A of lateral clamp 146A (alternately referred to herein as lateral pedicle rod clamp 146A) may swivel, rotate or rock within respective upper and lower beveled or angled lateral apertures 151A and 153A of left clamp body 134A (see FIGS. 11, 13 and description below). Lateral pedicle rod clamps 146 are for example sized to firmly and securely clamp a standard 5.5 mm straight or bent pedicle rod, although clamps 146 may also be sized to accommodate a range of rod diameters—for example, 6.35 or 6.25 mm pedicle rods. A central barrel or chamber 152A accepts a set screw or other fastener 154A (FIG. 7) for securing left upper and lower clamp halves/plates 136A and 138A together. In other words, one set screw 154A locks both medial and lateral swivel clamps 140A and 146A in place.

Left clamp body 134A includes a medial extension 156 supporting an acceptor 158. Acceptor 158 accepts an arm extension 160 of right clamp body 134B to facilitate securing left and right bodies 134A., 134B of pedicle clamp assembly 122 together (left clamp body 134A and right clamp body 134B) and to provide horizontal stability to system 100. In one aspect, acceptor 158 is a protrusion extending from an upper surface of medial extension 156 and having an aperture therethrough (FIG. 6) or a slot (FIG. 7) therein. The aperture or slot may be about parallel to medial extension 156. Arm extension 160 fits with acceptor 158, and acceptor 158 may be locked into place at a desired position along arm 160 via a set screw or other fastener 162 (FIG. 7).

Figure 11:
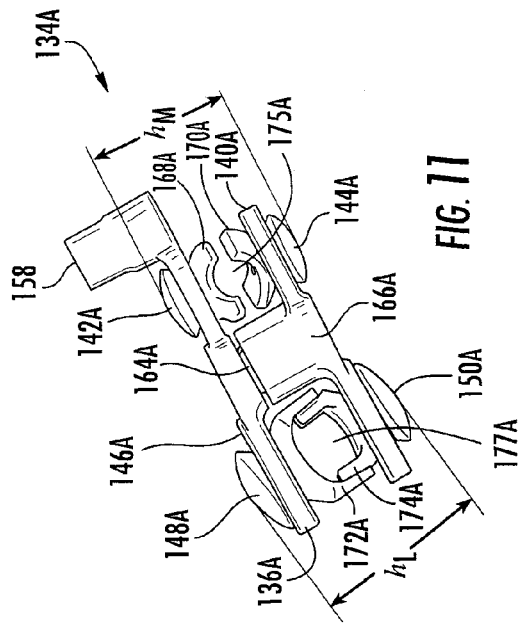
FIG. 11 is a side view of the alternate left pedicle clamp of FIG. 7.
Figure 10:
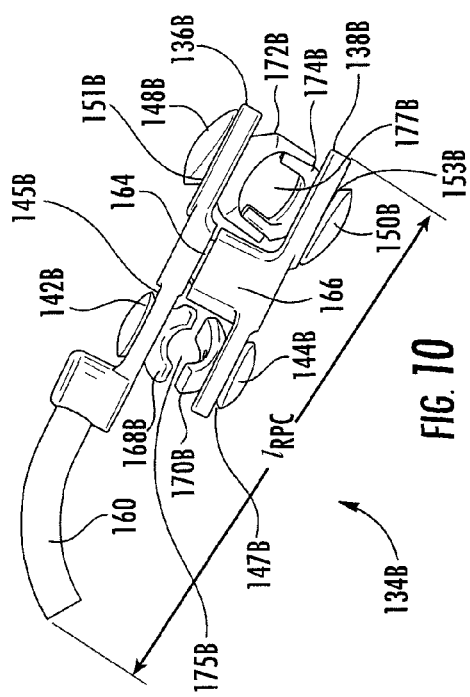
FIG. 10 is a side view of a right pedicle clamp of the fixation device of FIG. 7.
Figure 12:
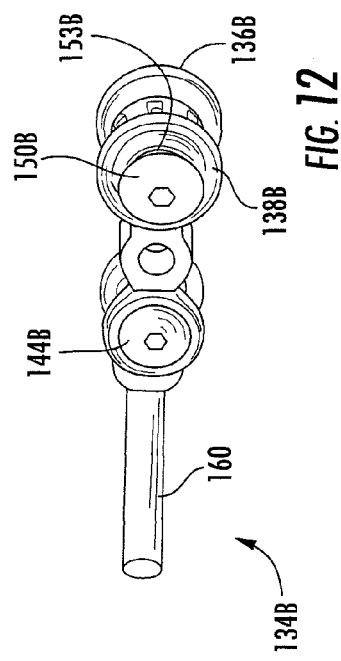
FIG. 12 is a bottom view of the right pedicle clamp of FIG. 10.

Features of right clamp body 134B are now described, primarily with respect to FIGS. 7, 10 and 12, which are best viewed together with the following description. Right clamp body 134B includes right upper and lower clamp halves or plates 136B and 138B. A right first or medial clamp 140B clamps right connecting rod 124B at or proximate a distal or posterior end of the rod. Right medial clamp 140B for example includes upper and lower heads 142B and 144B (FIG. 10) that may swivel, rotate or rock within respective upper and lower beveled or angled medial apertures 145B and 147B of right clamp body 134B (see FIGS. 11, 13 and description below). A right second or lateral clamp 146B includes right upper and lower clamp heads 148B and 150B (FIGS. 9 and 10) that grip a right/second pedicle rod 145B (i.e., a previously implanted rod) therebetween. As with medial clamp 140B, upper and lower heads 148B and 150B of right lateral clamp 146B (alternately referred to herein as lateral pedicle rod clamp 146B) may swivel, rotate or rock within respective upper and lower beveled or angled lateral apertures 151B and 153B of right clamp body 134B (see FIGS. 10, 12 and description below). A central barrel or chamber 152B accepts a set screw or other fastener 154B (FIG. 7) for securing right upper and lower clamp halves/plates 136B and 138B together.

Arm extension 160 extends from top clamp plate 136B of right clamp body 134B, proximate right medial clamp 140B. Arm extension 160 may arc or curve downward to facilitate connection with upward-facing acceptor 158 of left clamp body 134A.

As noted, upper and lower left clamp plates 136 and 138 may be joined together via set screw/fastener 154. However, clamp plates 136 and 138 may also include a plug and socket configuration to facilitate positioning of the halves together, prior to application of screw/fastener 154. For example, as illustrated with respect to FIG. 10 and right clamp body 134B, a plug 164 extends downward from right upper plate 136B. Plug 164 fits within an upward facing socket 166 of right lower plate 138B. Plug 164 may be a cylindrical plug to fit a cylindrical socket 166. A cylindrical plug and socket 164 and 166 may grant additional freedom of movement to right clamp body 134B, as upper and lower plates 136B and 138B may be rotated with respect to one another and still joined via plug and socket 164 and 166. Such freedom of movement may allow a surgeon to optimize fit of right clamp body 134B with patient anatomy. In another aspect, plug 164 may be shaped as a square, rectangle, hexagon or other geometric shape that requires a particular alignment to fit with a complementary socket 166. In yet another aspect, plug and socket 164 and 166 are cylindrical but include complimentary lock and key features. Providing plug 164 and socket 166 with complimentary shapes or lock and key features may maintain a desired alignment of upper and lower halves of right medial and lateral clamps 140B and 146B when right upper and lower clamp plates 136B and 138B are joined.

As shown with respect to FIG. 11, plug 164 and socket 166 may alternately or additionally be located with left clamp body 134A (see plug 164A and socket 166A).

As illustrated in FIGS. 9-11 and 14-18, medial or connecting rod clamps 140 and lateral or pedicle rod clamps 146 each include wings extending from the clamp heads and between upper and lower halves of the clamp bodies, forming swivel cups for accepting connecting rods 124 or pedicle rods 145, respectively. For example, referring to left clamp body 134A, opposing wings 168A extend downward from upper head 142A of medial clamp 140A and opposing wings 170A extend upward from lower head 144A of medial clamp 140A (see FIG. 11; for clarity, one wing 168A and one wing 170A are labeled). Opposing wings 172A extend downward from upper head 148A of lateral clamp 146A and opposing wings 174A extend upward from lower head 150A (FIG. 11; for clarity, one wing 172 and one wing 174 are labeled). As illustrated by angle a, FIG. 14, swivel cups of pedicle clamp assembly 122 have a flexibility window of approximately 20 degrees in any direction. This angulation provides added system flexibility and prevents concentration of stress at attachment and clamping surfaces. Swivel cups additionally allow pedicle clamps 146 and connecting rod clamps 140 to take on multiple orientations while still exerting a radial clamping force on pedicle rods 145 and connecting rods 124 (respectively).

With respect to right clamp body 134B, opposing wings 168B extend downward from upper head 142B of medial clamp 140B and opposing wings 170B extend upward from lower head 144B of medial clamp 140B. Opposing wings 172B extend downward from upper head 148B of lateral clamp 146B, and opposing wings 174B extend upward from lower head 150B of lateral clamp 146B (see FIG. 11; for clarity, one each of wings 168B-174B are labeled).

Opposing wings 168 and 170 and opposing wings 172 and 174 are shaped to form a cylindrical cavity 175/177 for fitting connecting rods 124 therebetween when lateral pedicle rod clamp 146 is attached to a pedicle rod 145. In one aspect, opposing wings 168 and 170 overlap (see e.g., FIGS. 10 and 11). In another aspect, shown in FIGS. 8, 9, 17 and 18, lateral overlapping wings 168 and 170/172 and 174 secure together via lock and key features. For example, wing 168 fits over wing 170 such that a tab extension 176 of wing 170 rides within a channel 178 of wing 168. Tab 176 and channel 178 facilitate aligning and securing lateral clamp 146 about a pedicle rod 145. Although tab extension 176 and channel 178 are shown and described with respect to left lateral clamp 146A, such lock and key features may also be incorporated into wings 172 and 174 of right lateral clamp 146B.

Tab extensions 176 beneficially allow a surgeon to align and loosely fix pedicle rod swivel cups/clamps 146 about pedicle rods 145 and then maneuver the entire pedicle clamp assembly 122 towards connecting rods 124. To prevent upper and lower pedicle clamp assembly plates 136 and 138 from rotating about one another, socket 166 and plug 164 may have complementary lock-and-key features. For example, plug and socket 164 and 166 may be square. Dimples 186 accept a tool to allow centering of swivel cups/clamps 146 while pedicle clamp assembly 122 is installed.

As illustrated, right pedicle clamp 134B has a length $l_{RPC}$ (FIG. 10) of about 62-63 mm. Left pedicle clamp 134A has a lateral clamp height $h_L$ of about 19-20 mm, a medial clamp height $h_M$ of about 15-16 mm, a lateral clamp width $w_L$ of about 14 mm and a medial clamp width $w_M$ of about 11-12 mm. See FIGS. 10, 11 and 13. However, length $L_{RPC}$ may vary based upon size demands of system 100.

Figure 14:
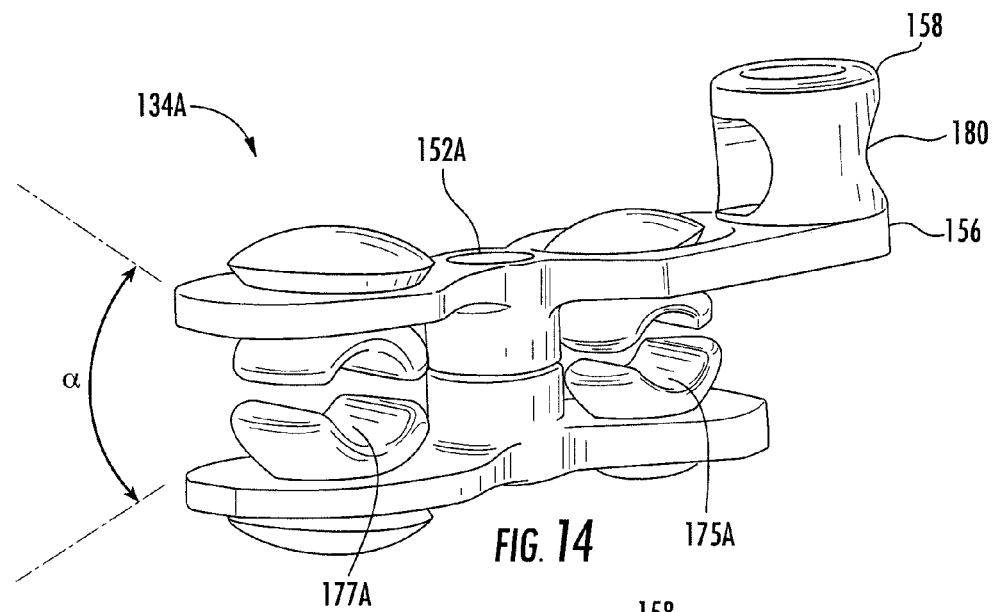
FIG. 14 is a side perspective view of the left pedicle clamp of FIG. 6.

As illustrated by angle a, FIG. 14, swivel heads of pedicle clamps 146 allow for approximately 20 degrees of freedom in all directions when adjusting position of assembly 122 on pedicle rods 124.

Figure 15:
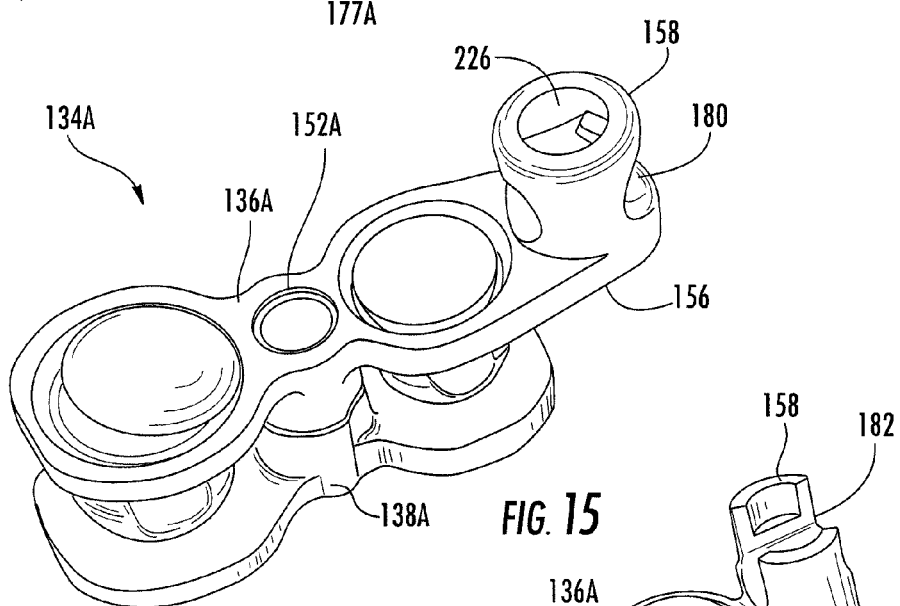
FIG. 15 is a top perspective view of the left pedicle clamp of FIGS. 6 and 14.
Figure 16:
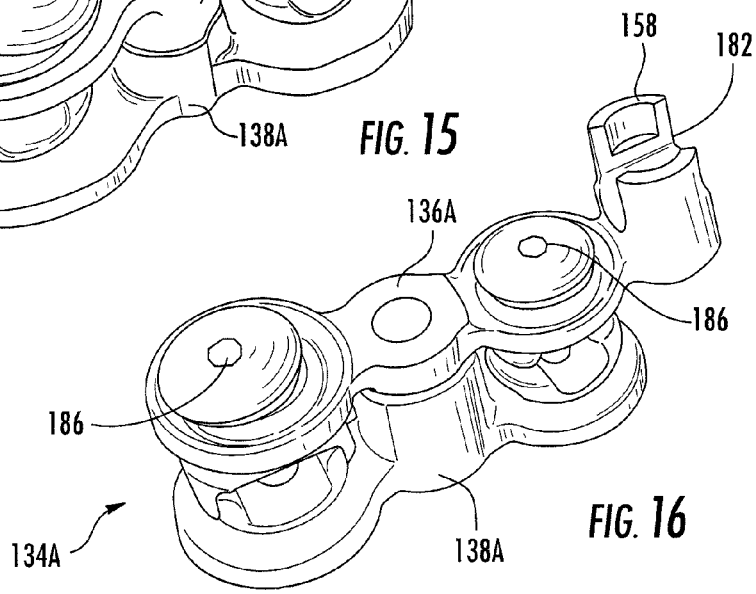
FIG. 16 is a top perspective view of the left pedicle clamp of FIGS. 7, 11 and 13.
Figure 17:
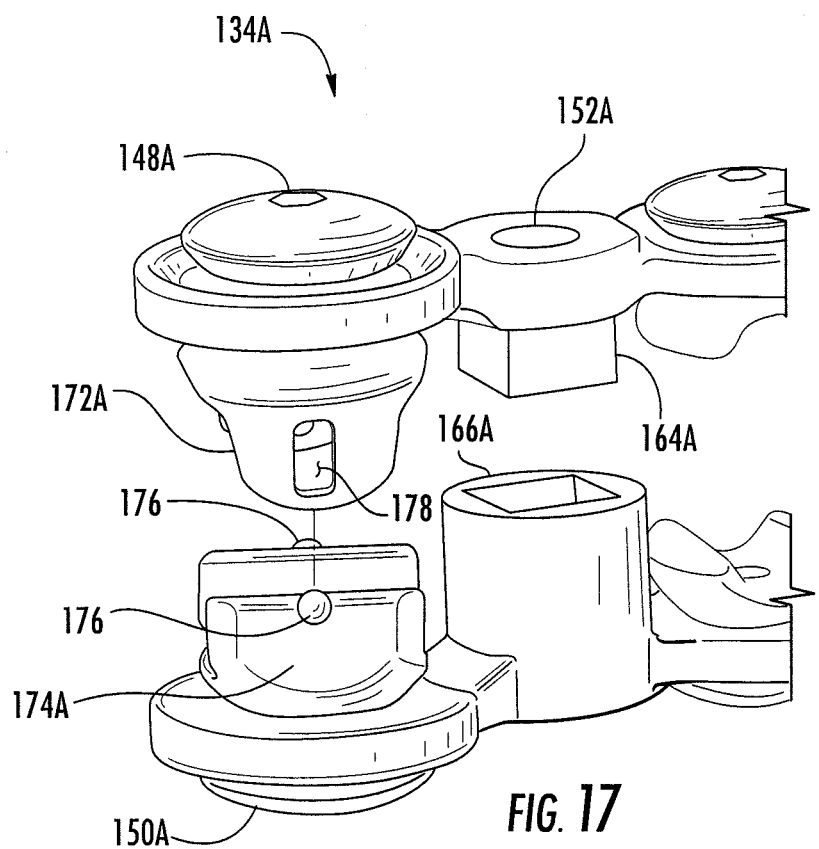
FIG. 17 is a side perspective view showing upper and lower halves of a left pedicle clamp, with the lower clamp heads including securing tab extensions for joining with the upper clamp heads, according to an embodiment.
Figure 18:
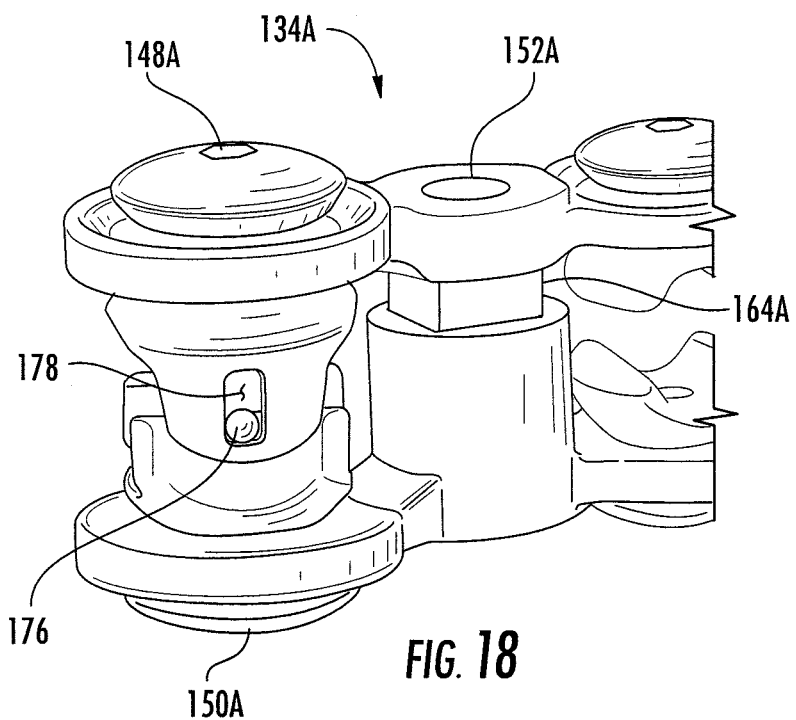
FIG. 18 is a side perspective view showing the upper and lower clamp heads of the left clamp of FIG. 17 joined via the tab extensions.

FIGS. 15 and 16 show alternate embodiments of left clamp body 134A. FIG. 15 shows left clamp body 134A with acceptor 158 having a side-to-side aperture 180. Aperture 180 is replaced by a top slot 182, in FIG. 16. Where acceptor 158 includes aperture 180 (FIG. 15), arm extension 160 of right clamp body 134B slides into aperture 180 and acceptor 158 is secured at a desired position along arm extension 160 via a set screw or other locking component inserted in an upper channel 184 of acceptor 158 (i.e., with set screw 162). Where acceptor 160 includes top slot 182 (FIG. 16), arm extension 160 may be pressed into slot 182, or clamp bodies 134A and 134B may be pressed together to introduce arm extension 160 into slot 182. In one example of installation, pedicle clamps 146 are first loosely attached to pedicle rods 145, using tabs 176 to hold clamps 146 in place. Pedicle clamp assembly 122 is maneuvered towards connector rods 124, and then left and right halves of pedicle clamp assembly 122 are connected by pressing arm extension 160 into top slot 182. Arm extension 160 is for example secured within slot 182 by placing a set screw into acceptor 158, over arm extension 160, and clamps 140 and 146 are secured together with set screws 154. Thus, it will be appreciated that inner walls of acceptor 158 and inner walls of chambers 152 may be threaded to complement threads of a set screw (i.e., a threaded set screw 162/152). It will also be appreciated that alternate geometries of upper and lower plates 136 and 138 (other than those shown in FIGS. 15 and 16) are within the scope hereof.

Select or all of clamp heads 104, 144, 146, 150, 152, 172, 174, 178 and 180 may include central sockets or dimples 186, into which placement tools may be inserted to adjust angle (swivel) of the clamp heads. For example, it may be useful while placing device 100 with a patient's spine to use a tool to adjust position of clamp heads 104 upon the spinous process, clamp heads 142 upon connectors 124 or clamp head 148 or 150 upon existing pedicle rods 145.

Figure 19:
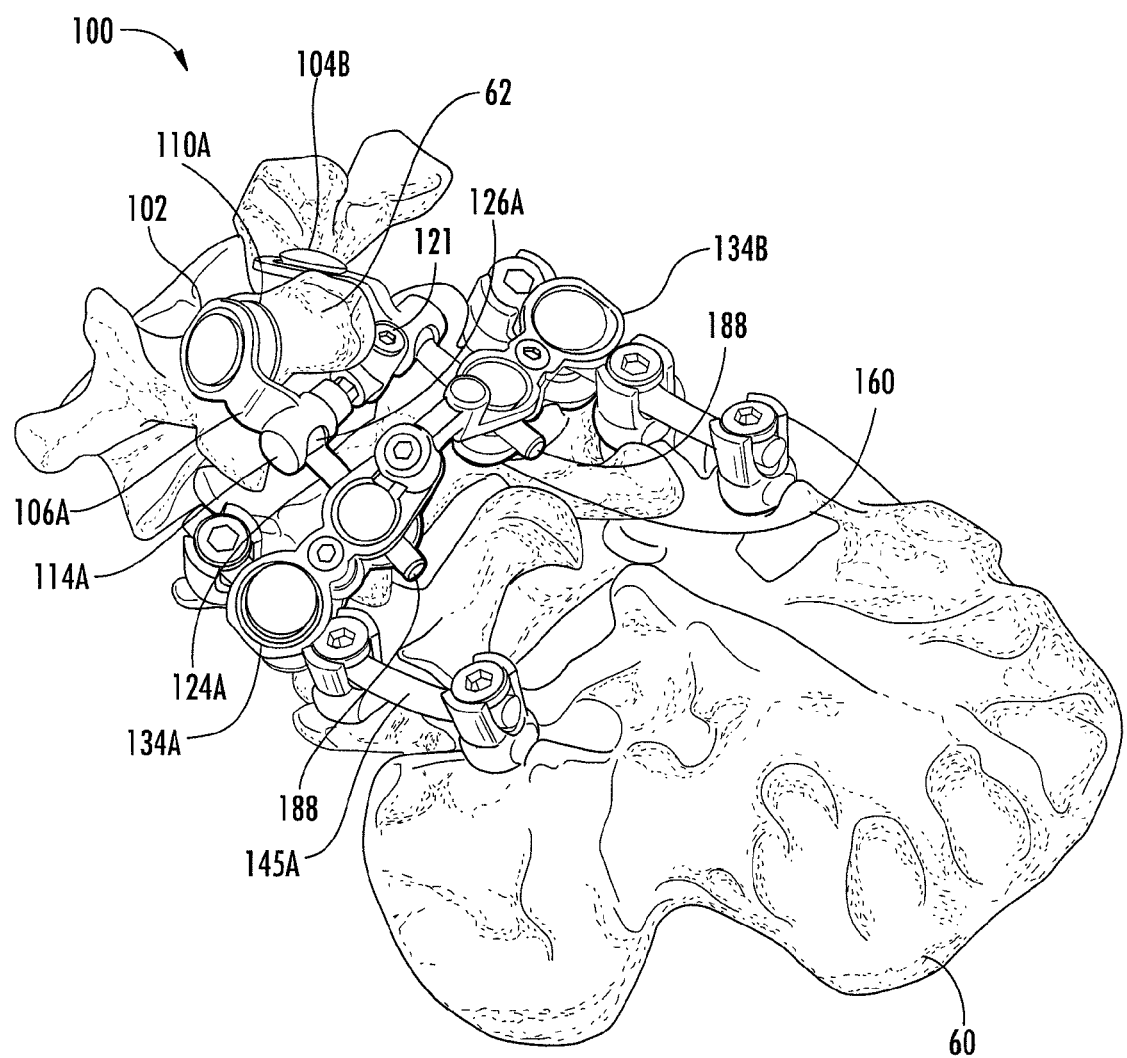
FIG. 19 is a top to side perspective view showing the spinal fixation device of FIG. 6, mounted with a segment of a model human spine and showing the pedicle clamp system attached proximate ends of the connecting rods, according to an embodiment.
Figure 20:
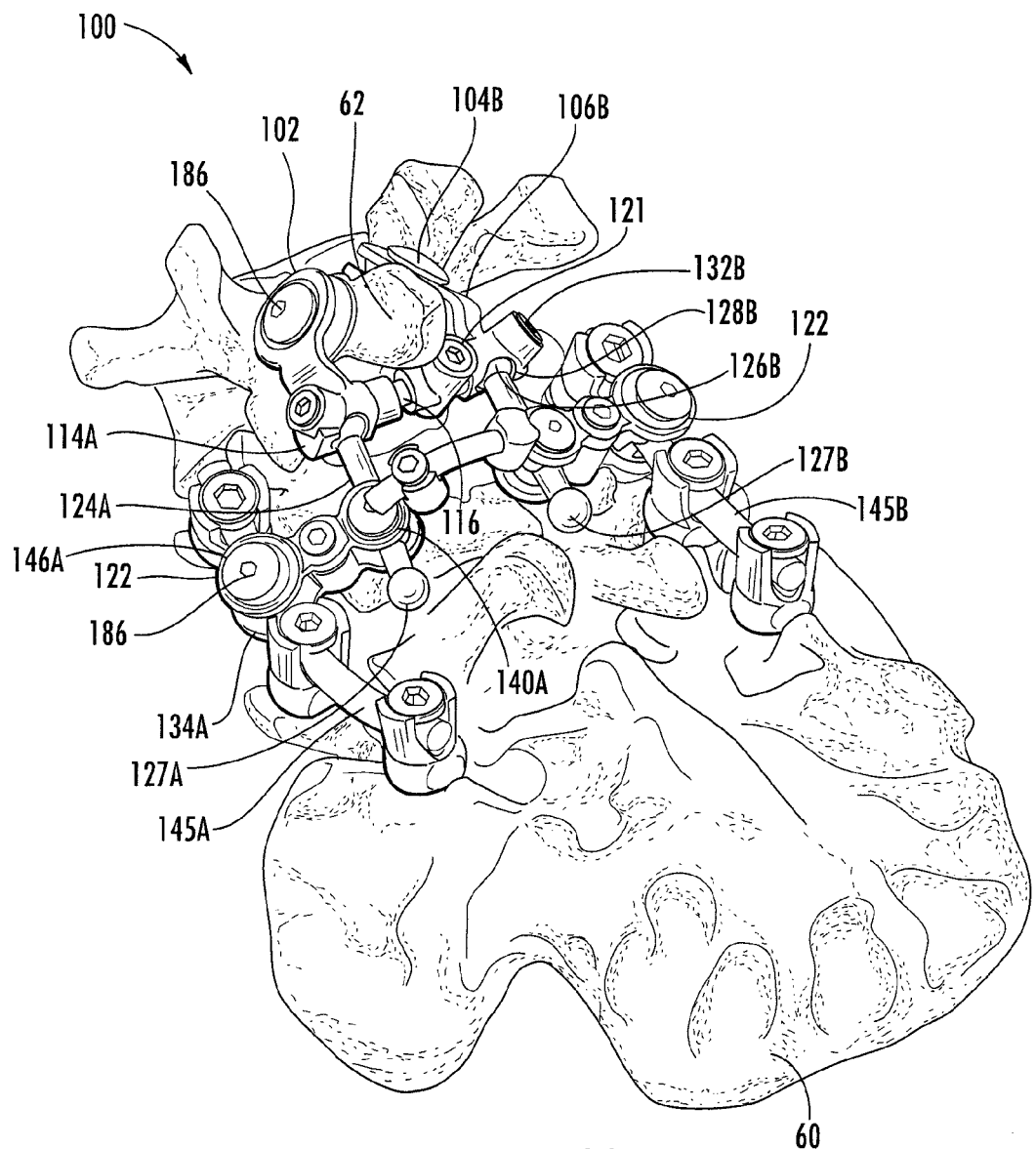
FIG. 20 is a top to side perspective view of a spinal fixation device similar to that of FIGS. 7 and 19, showing connecting rods with ball ends as shown in FIGS. 3-4, according to an embodiment.
Figure 21:
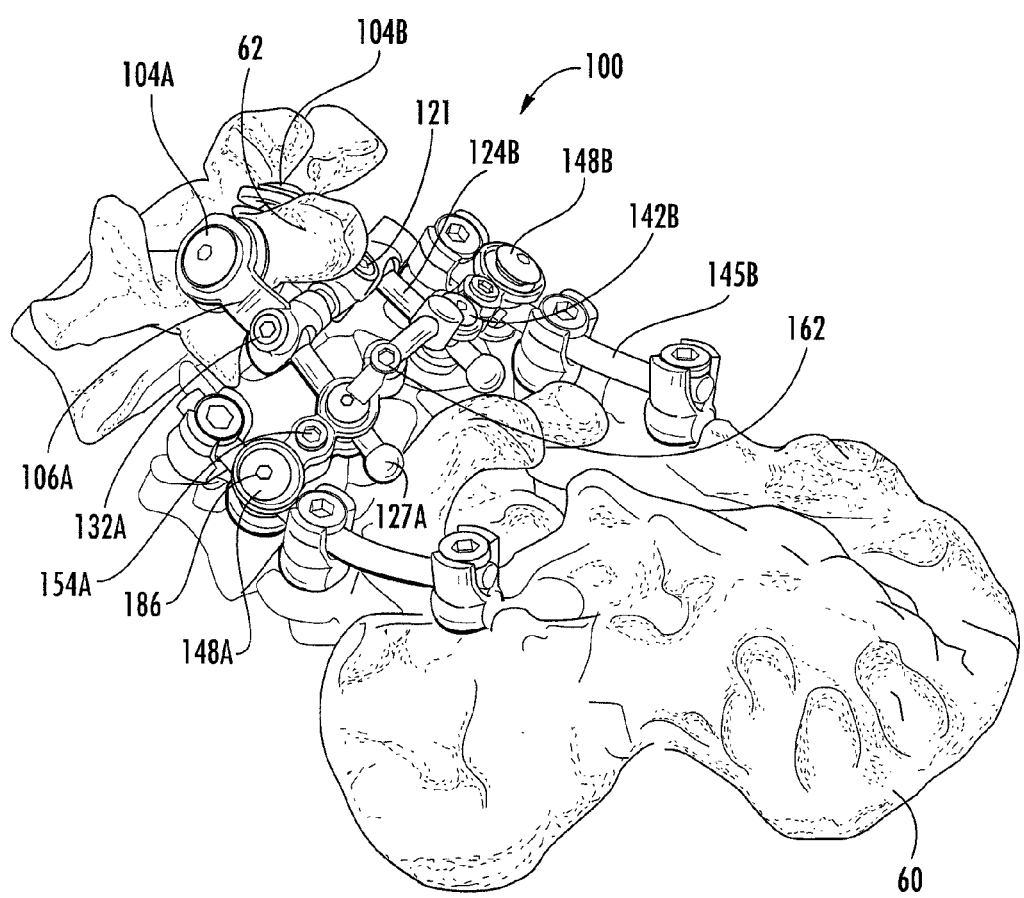
FIG. 21 is an alternate top, perspective view of the spinal fixation device of FIG. 20.

As described above, connecting rods 124 may terminate in distal ball ends 127. Alternately, connecting rods 124 may terminate opposite ball ends 126 in straight ends 188. Compare, for example, straight ends 188 depicted in FIG. 19 with distal ball ends 127 as shown in FIGS. 20 and 21.

Swivel clamps 104, 140 and 146, ball and socket joints 130, curved clamp arms 106, curvature of arm extension 160 and raised acceptor 158 facilitate custom-fitting of spinal fixation system 100 to a patient's anatomy. For example, system 100 may be made longer, shorter, narrower or wider by varying angles and distance between halves 103A and 103B of spinous clamp section 102, by varying angles and distance between spinous clamp section 102 and pedicle clamp assembly 122 and/or by varying angles and distance between left and right clamp bodies 134A and 134B of pedicle clamp assembly 122. Thus, system 100 may be spaced closer to or farther from a patient's spine, and may rotate or swivel along multiple points to expand, contract or otherwise adjust to provide a best fit to existing hardware and patient anatomy. Ball and socket joints 130 allow pedicle clamp system 122 to be set narrower (by sliding arm extension 160 further into acceptor 158) or wider (by settling a distal portion or an end of arm extension 160 into acceptor 158). Joints 130 also allow connectors 124 to be raised, lowered and/or tilted from ball ends 126 to distal ball ends 127 or distal straight ends 188 to connect with a pedicle clamp system 122 that must be relatively higher or lower than clamp section 102 on one or both sides, and/or which tilted laterally to one side or the other with respect to clamp section 102. Connecting rods 124 may be adjusted into a v-shape to facilitate a narrow pedicle clamp system 122. Arm extension 160 may be grasped distally or at its end by acceptor 158 to approximate an a-shape if a wider pedicle clamp system 122 is needed. Rods 124 may also be adjusted to one side, as shown in FIG. 20, to accommodate spinal curvature. Rods 124 may also be adjusted away from or towards the spine to accommodate other variations in spinal anatomy. It will be appreciated that ball and socket joints 130 allow adjustment of system 100 to a wide variety of positions. System 100 is therefore ideal for spinal arthrodesis cases, in which bone size, bone quality and amount of bone removed during previous procedures varies from one patient to another, as do spacing, size and orientation of existing pedicle rod constructs.

The ability of system 100 to clamp onto an existing pedicle rod construct beneficially allows for a less invasive device and for less invasive implantation. System 100 may for example be secured with a patient's spine and existing pedicle rod construct through an incision of about 2 cm. The further ability to implant system 100 without adjusting the existing pedicle rod and screw construct also reduces invasiveness of implantation.

In practice, device 100 is generally attached below the spinous process midline near the lamina-spinous junction where bone cross section is the largest. Clamps 104 are positioned as desired (i.e., via a tool inserted into dimples 186, by adjusting distance between clamp halves 103 by adjusting the fit of shaft 116 within channel 118, and by rotating clamp section 102 at ball and socket joints 130) and tightened to secure spinous process clamp section 102 in the desired orientation. System 100 provides at least 5 degrees range of motion in all three axes (x, y and z) to allow enough flexibility for installation. Range of motion of system 100 may be reduced, for example to less than 5 degrees, by tightening system 100 (e.g., at screws/fasteners 132, 121, 154, 162) once placed. Some limited range of motion of system 100 when implanted may reduce or prevent stress concentration at attachment points or joints. System 100 allows limited motion at swivel or ball-and socket joints, and, by locking complementary metal portions together (e.g., locking shaft 116 within channel 118 and arm extension 160 within acceptor 158), may prevent sliding metal-on-metal surfaces, thus additionally reducing device wear. System 100 may be made from medical grade titanium—for example, grade 5 Ti4Al6V or another sufficiently strong biocompatible material to further insure device longevity. Construction and cross-linking of device 100 also aids in withstanding vertical, lateral, compressive and rotational forces imparted by flexion, extension, lateral bending and torsion/rotation of adjacent motion segments.

Adjustment of rods 124 at ball and socket joints allows rods 124 to be moved up, down, laterally and/or vertically to best fit spinous process clamp section 102 with existing pedicle rods 145. Adjustability of arm extension 160 within acceptor 158, in connection with adjustability of rod 124 angles allows for pedicle clamp assembly 122 to be made narrower or wider, raised or lowered, shifted or straight (with respect to the plane of spinous process clamp section 102). Likewise, curvature of pedicle clamp assembly may be altered by adjusting position of arm extension 160 within acceptor 158, where arm extension 160 is curved. Adjustability of upper clamp heads 142 and 148 and lower clamp heads 144 and 150 lends to additional adjustability of system 100.

Proposed Device Installation

The following steps illustrate exemplary installation of device 100. A laminectomy removing the posterior spinous process may be required to accommodate cross-connecting pedicle clamp assembly 122. A distraction tool will be needed during the installation process.

Initially, an incision is made in the midline along the lumbar spine of the patient. An incision is made through the intraspinous ligament using a cannulated tool. Distraction of the adjacent levels may be achieved using a separate distraction tool. Decortication of the spinous process around the area of insertion and trimming of additional bone tissue might be required to accommodate system 100. Left half 103A of spinous clamp section 102 is placed on the left side of the lamina-spinous junction of the adjacent spinous process and the swivel clamp (clamp head 104A, clamping face 110A, spikes 112) is allowed to roll slightly for best orientation with the spinous process prior to clamping. Right half 103B is next placed with the left half of the lamina-spinous junction in like manner, and the two clamps halves 103A and 103B are compressed using a compression tool and then locked together. Connecting rods 124 are allowed to freely rotate in ball-and-socket joints 130 while clamp section 102 is installed about the spinous process. Left pedicle clamp 134A is then placed over and aligned with left pedicle rod 145A, i.e., using a tool inserted into dimple 186 on head 148A. The tool may be torqued or clamp 134A otherwise manipulated, for example by torqueing locking screw/set screw 154A, until locking tab 176 enters slot 178 of the upper swivel cup (clamp head 148A and attached wings 172A), thus loosely docking clamp 134A to pedicle rod 145A.

Left pedicle clamp 134A is then maneuvered towards left connecting rod 124A, following which a different tool is used to laterally slide rod 124A into channel 175A between upper and lower medial wings 168A and 170A. Locking screw 154A is torqued again to secure connecting rod 124A without fully locking left clamp body 134A. Left clamp body now secures pedicle rod 145A and connecting rod 124A without fully clamping them in place.

The above maneuvering and securing is repeated for right pedicle clamp 134B (about pedicle rod 145B and connecting rod 124B). Arm extension 160 is next maneuvered into slot 182 of acceptor 158 and locking/set screw 162 is inserted into acceptor 158 and fully tightened. Locking/set screws 154A and 154B are then fully torqued, and locking/set screws 132A and 132B are fully tightened to immobilize ball-and-socket joints 130.

Figure 22:
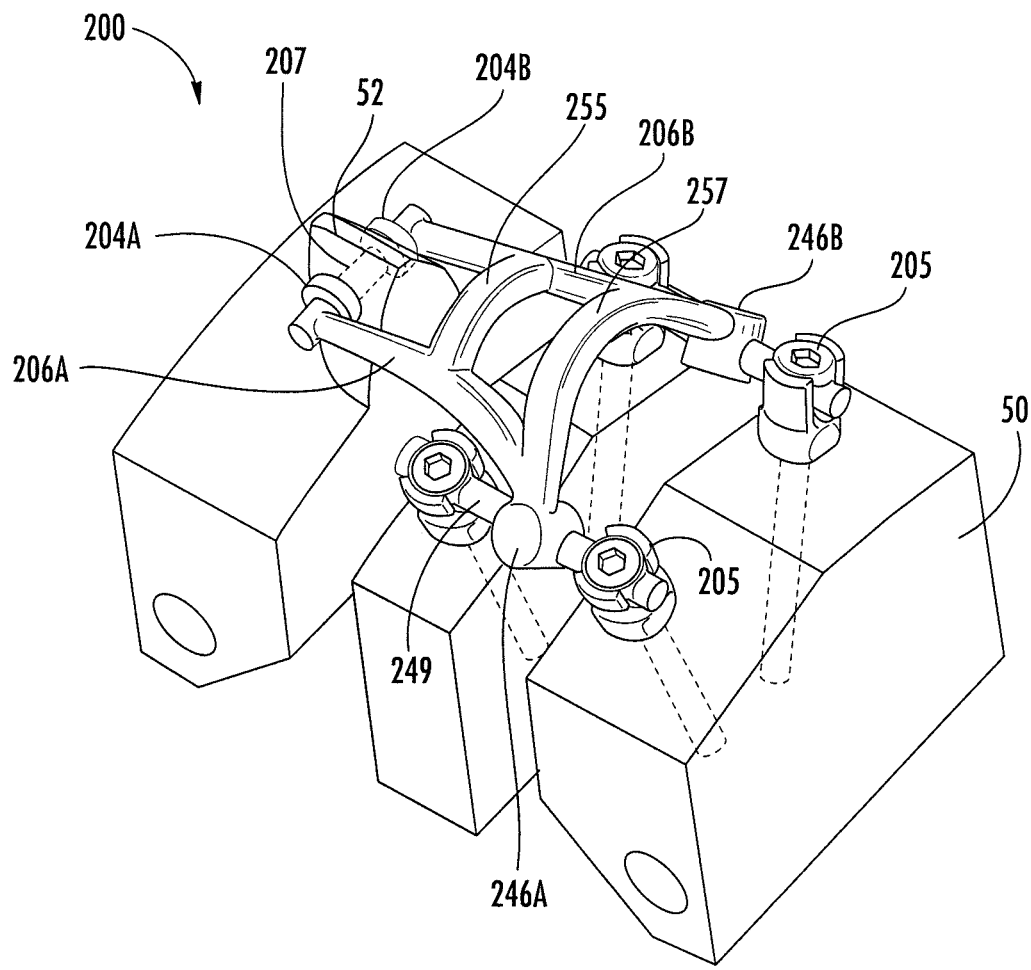
FIG. 22 is a top, perspective view of a spinous process fixation device that is secured through the spinous process and connects to an existing rod and screw system, according to an embodiment.

FIGS. 22-29 show spinal fixation systems 200-600 on model ASTM blocks 50 and model human spine segments 60. In particular, FIG. 22 shows a simplified, conceptual fixation system model 200 and illustrates fixation of a mock spinous process 52 adjacent to an existing pedicle rod and screw construct 205, which includes straight pedicle rods 249. Rods 249 are for example standard 5 mm pedicle rods fixed at each end by pedicle screws. For ease of illustration, only one pedicle rod 249 is numbered. Opposing clamp heads 204 extending from opposing arms 206 grasp mock spinous process 52 therebetween. As shown in conceptual FIG. 22, heads 204 fix process 52 via a penetrating rod or screw 207; however, penetration of a spinous process is avoided in system 100 and other designs, in order to reduce invasiveness of the spinal fixation system and to reduce metal-on-bone wearing surfaces that may be especially vulnerable to stress during flexion and extension moments applied to the spinous process.

Arms 206 curve outward from heads 204 to pedicle rod clamps 246, and are connected by upward-curving cross members 255 and 257, which provide space for spinal features beneath model 200.

Figure 23:
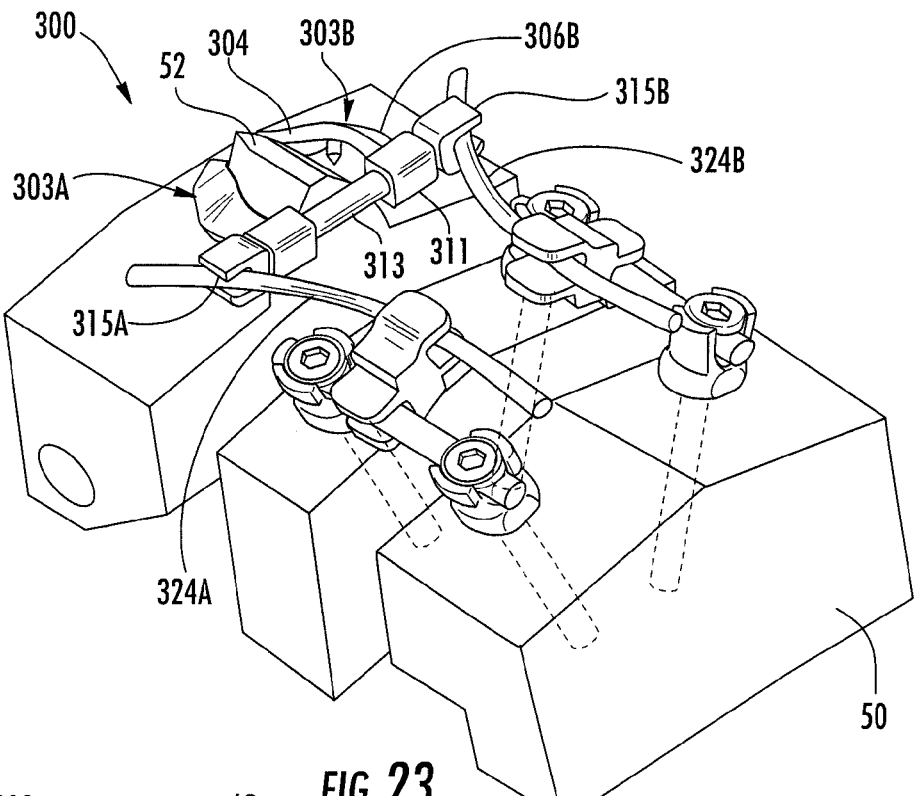
FIG. 23 is a top perspective view of a spinal fixation system including a spinous process clamp, dual pedicle rod clamps and a pair of "bent v" shaped rods connecting the spinous process clamp and pedicle rod clamps, according to an embodiment.
Figure 24:
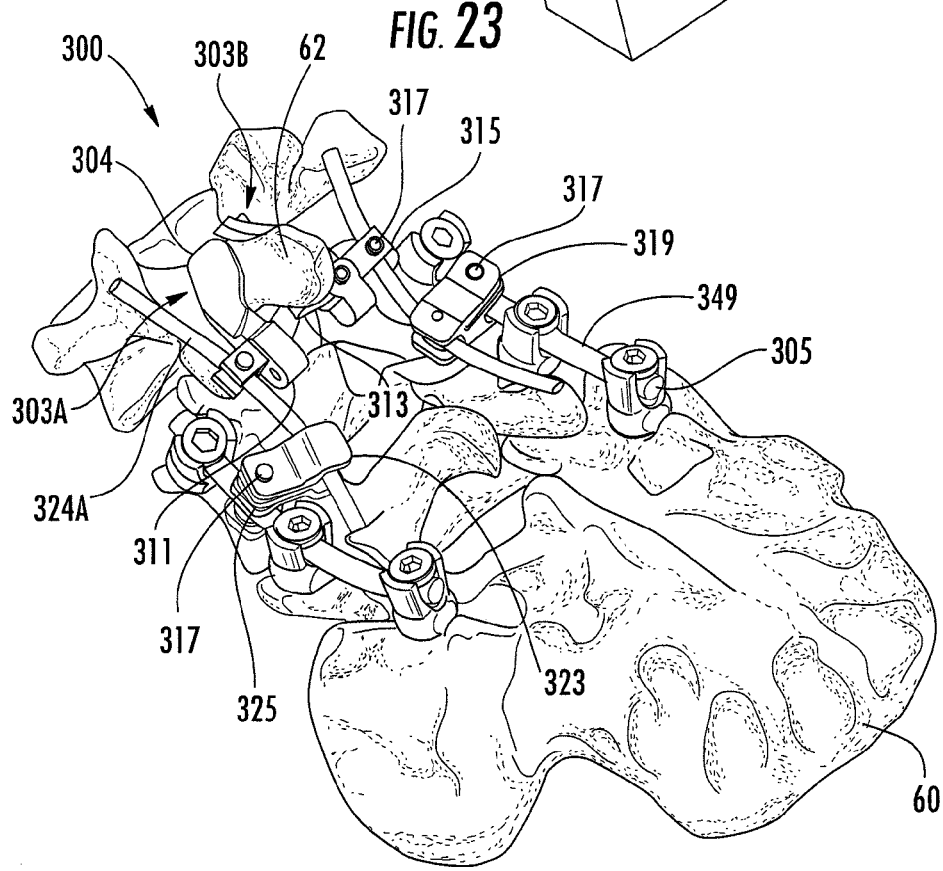
FIG. 24 is a top perspective view of the spinal fixation system of FIG. 23 mounted with a model human spinal segment.

FIGS. 23 and 24 show a v-shaped bend rod spinal fixation system 300 mounted with ASTM blocks 50 and a model spinal segment 60, respectively. FIGS. 23 and 24 are best viewed together with the following description.

System 300 includes a spinous clamp 302, having one clamp half 303 mounted with each of two opposing, curved clamp arms 306. Arms 306 terminate on one end in heads 302 and in acceptors 311 on an opposite end. Acceptors 311 include inner channels (not shown) to accept a mid-bar 313. A clamp-to-clamp distance of mid-bar 313 may be adjusted by sliding clamp halves 303A and 303B closer together or farther apart along mid-bar 313. Mid-bar 313 connects with or forms a connecting rod clamp 315 on either side. Connecting rod clamps 315 may be locked in place along a curved connecting rod 324 using a single pin or screw 317. Likewise, a pin or screw 317 may be used to secure acceptors 311 in place along mid-bar 313 (see FIG. 24). Although not shown, clamp heads 304 may have spiked faces similar to those of clamp heads 104, to enhance security of clamp heads 104 within spinous process bone.

Stacked clamps 319 join with and secure rods 324 farther along the length of the rods. Stacked clamps 319 include medial, inward-facing rod clamps 323 and lateral, outward-facing pedicle clamps 325, which clamp onto an existing pedicle rod 349 of a pedicle rod and screw construct 305. System 300 is therefore able to "piggyback" onto an existing pedicle-rod construct. Stacked clamps 319 rotate up or down to allow adjustment of system 300 to fit the individual spinal anatomy of a patient. Likewise, swivel clamps or cups on spinous clamp 304 (not shown, see, e.g., FIGS. 3 and 4) provide a third degree of freedom to adjust system 300 to individual anatomy. Stacked clamps 319 may be secured in place with only one pin or screw 317 each, as shown in FIG. 24. It will be appreciated that although not shown in FIGS. 23 and 24, a cross-bar may be added between or proximate stacked clamps 319 for additional stability and/or to relieve stress and fatigue on system 300.

Figure 25:
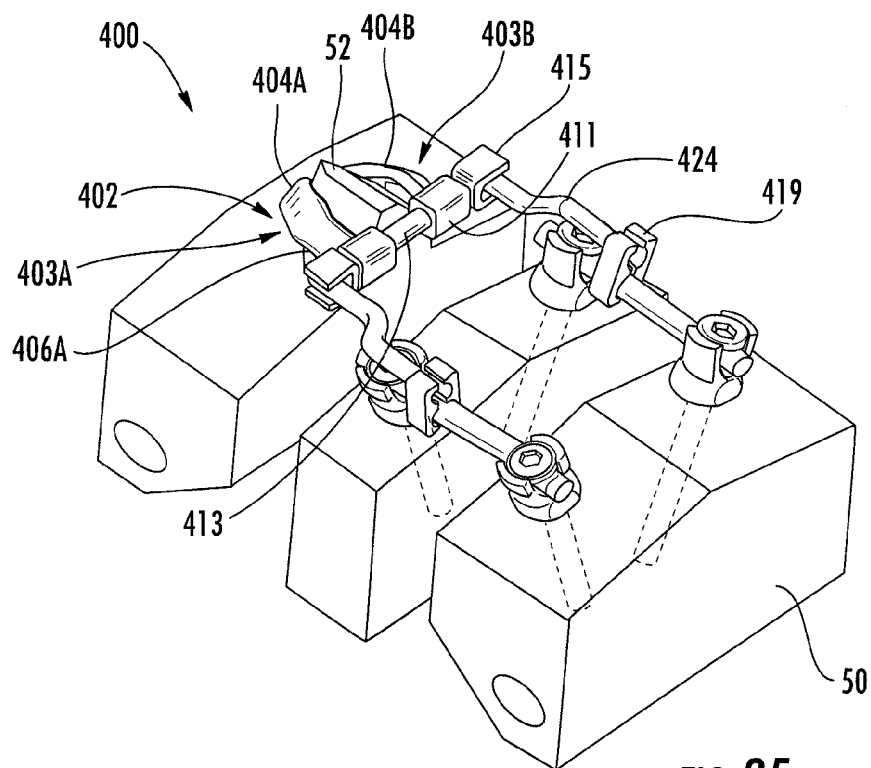
FIG. 25 is a top perspective view of a spinal fixation system including a spinous process clamp, dual pedicle rod clamps and a pair of "s"-shaped rods connecting the spinous process clamp with the pedicle rod clamps, according to an embodiment.
Figure 26:
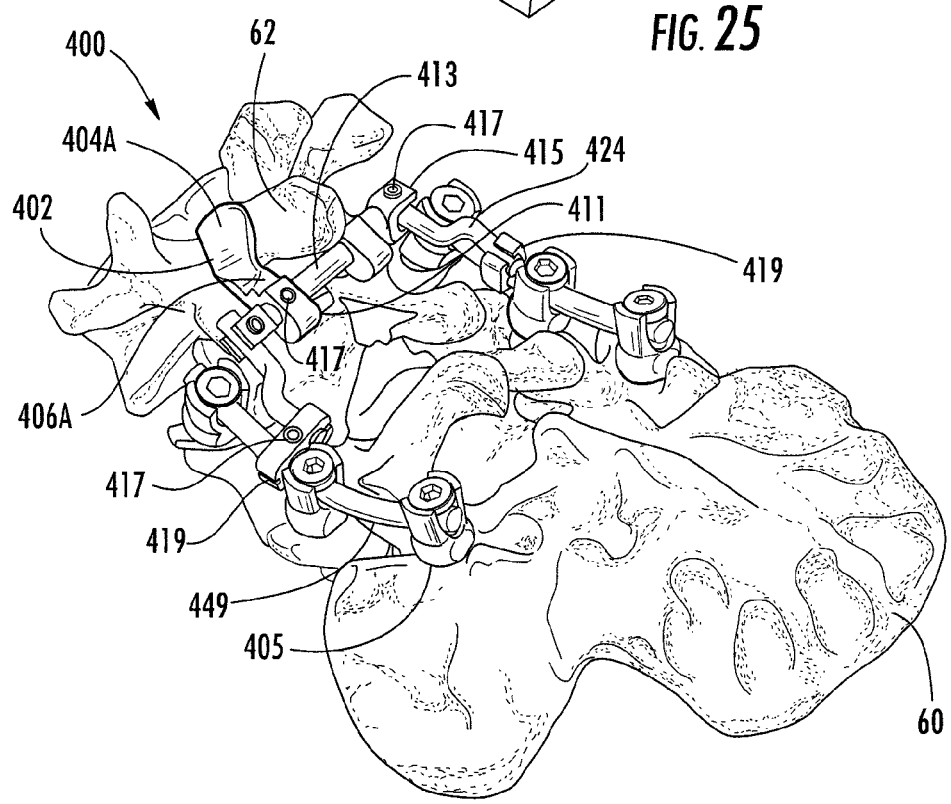
FIG. 26 is a top perspective view of the spinal fixation system of FIG. 25 mounted with a model human spinal segment.

FIGS. 25 and 26 show a spinal fixation system 400, on ASTM blocks 50 and a model spinal segment 60, respectively. System 400 includes a spinous clamp 402, having one clamp half 403 mounted with each of two opposing, curved clamp arms 406. Opposing clamp heads 404 mount with or are formed with arms 406. Arms 406 terminate opposite heads 404 in acceptors 411, which have channels (not shown) running through to accept a mid-bar 413. A clamp-to-clamp distance of mid-bar 413 may be adjusted by sliding clamp halves 403A and 403B closer together or farther apart along mid-bar 413. Mid-bar 413 connects with or forms a connecting rod clamp 415 on either side. Connecting rod clamps 415 may be locked in place along a connecting rod using a single pin or screw 417. Likewise, a pin or screw 417 may be used to secure acceptors 411 in place along mid-bar 413 (see FIG. 24).

System 400 is similar to system 300, but utilizes s-shaped connector rods 424 in place of curved rods 324, and employs lateral pedicle rod clamps 419 that clamp to s-rods 424 on one side (i.e., via a top clamp 423) and to existing pedicle rods 449 of an existing pedicle rod system 405 on an opposing side (i.e., via a bottom clamp 425). System 400 is therefore able to "piggyback" onto an existing pedicle-rod construct. Clamps 419 may rotate slightly up or down in response to rotation of mid-bar 413, and therefore lend some flexibility to the final, locked orientation of system 400. S-shaped connector rods 424 add additional flexibility to system 400. Swivel clamps or cups on spinous clamp 402 (not shown, see, e.g., FIGS. 3 and 4) and rotation of acceptors 411 about mid-bar 413 may provide further freedom of movement to adjust system 400 to individual anatomy. Clamps 419 may be secured in place with only one pin or screw 417 each, as shown in FIG. 26. It will be appreciated that although not shown in FIGS. 25 and 26, a cross-bar may be added between or proximate clamps 419 for additional stability and/or to relieve stress and fatigue on system 400.

Figure 27:
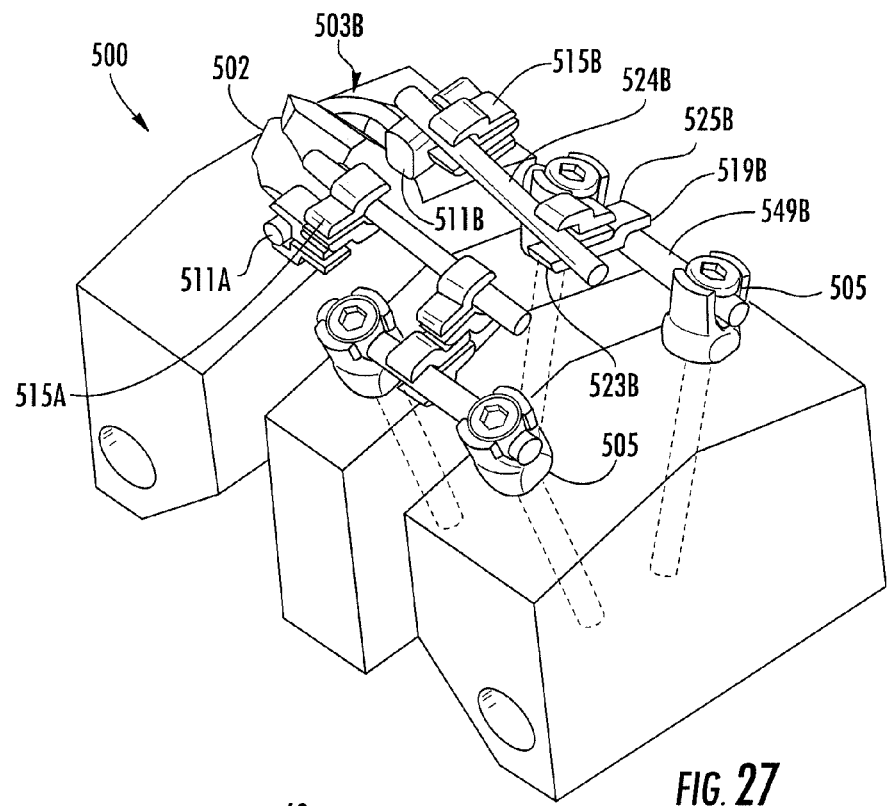
FIG. 27 is a top perspective view of a spinal fixation system including a spinous process clamp, dual pedicle rod clamps and a pair of "straight v"-shaped rods connecting the spinous process clamp with the pedicle rod clamps, according to an embodiment.
Figure 28:
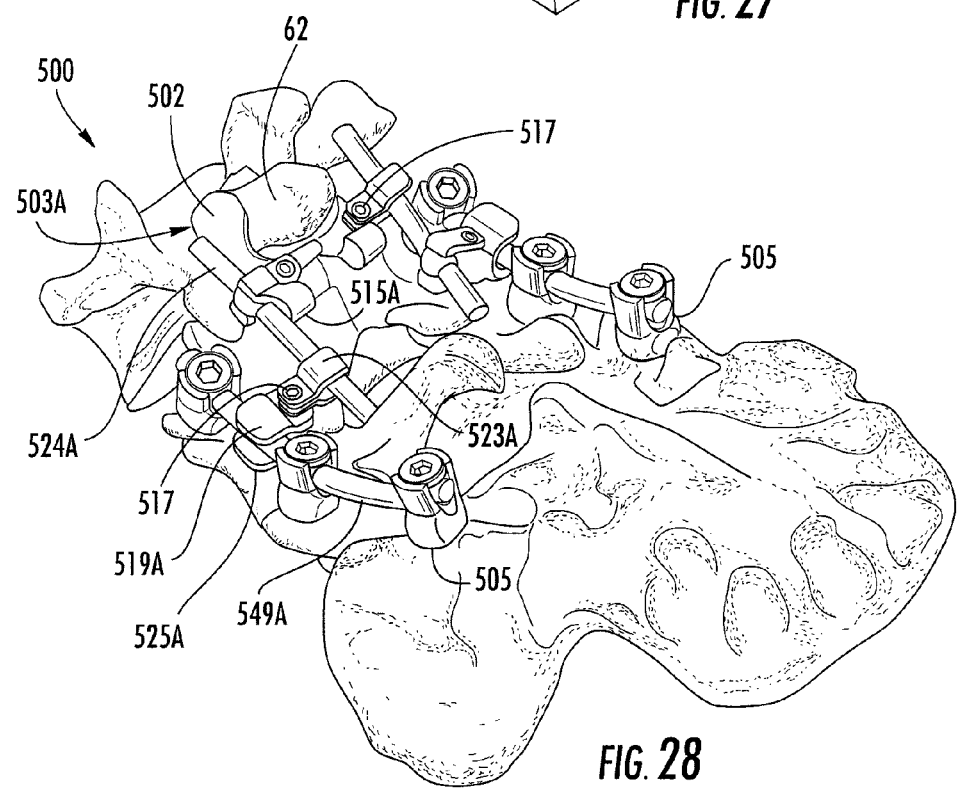
FIG. 28 is a top perspective view of the spinal fixation system of FIG. 27 mounted with a model human spinal segment.

FIGS. 27 and 28 illustrate a spinous process fixation system 500, which also attaches to an existing pedicle rod and screw construct. System 500 includes a spinous clamp 502, having one clamp half 503 mounted with each of two opposing, curved clamp arms 506. Arms 506 terminate on one end in heads 502, which may include swivel heads and/or bone interface teeth, as shown and described with respect to system 100. Arms 506 terminate opposite heads 502 in bilateral protrusions 511. Detachable stacked clamps 515A, 515B may be attached to protrusions 511 at one side, and simultaneously clamped to connecting rods 524 at an opposing sides. Ball-like features between the opposing sides of stacked clamps 515 permit position and angles within clamps 515 to be customized to increase the range of angles between arms 506 and connecting rods 524, and between connecting rods 524 and existing pedicle rods 529. Detachable stacked clamps 515 may be locked in place along connecting rod 524 using a single pin or screw 517, as shown in FIG. 28. Pre-existing, straight 4.5 mm pedicle rods may be used as connecting rods 524.

System 500 employs stacked clamps 519 to join and secure rods 524 with existing pedicle rods 549. Stacked clamps 519 are similar to clamps 319, and include medial, inward-facing rod clamps 523 for clamping connecting rods 524 and lateral, outward-facing pedicle clamps 525 for clamping pedicle rods 549. Like detachable stacked clamps 515, stacked clamps 519 may include internal ball features that permit variation of angles between inner and outer clamp faces, and therefore increase permissible angles and orientation of connecting rods 524. For example, the rods may rotate up, down, in, out or sideways. Thus, system 500 is customizable to the spinal anatomy of an individual patient. Stacked clamps 519 may be secured in place with only one pin or screw 517 each, as shown in FIG. 28. It will be appreciated that although not shown in FIGS. 27 and 28, a cross-bar may be added between or proximate stacked clamps 519 for additional stability and/or to relieve stress and fatigue on system 500. Stacked clamps 515 and 519 may be interchanged as spinous clamp—cross connector attachments or as cross connector—pedicle rod attachments, thus reducing the number of different parts needed.

Figure 29:
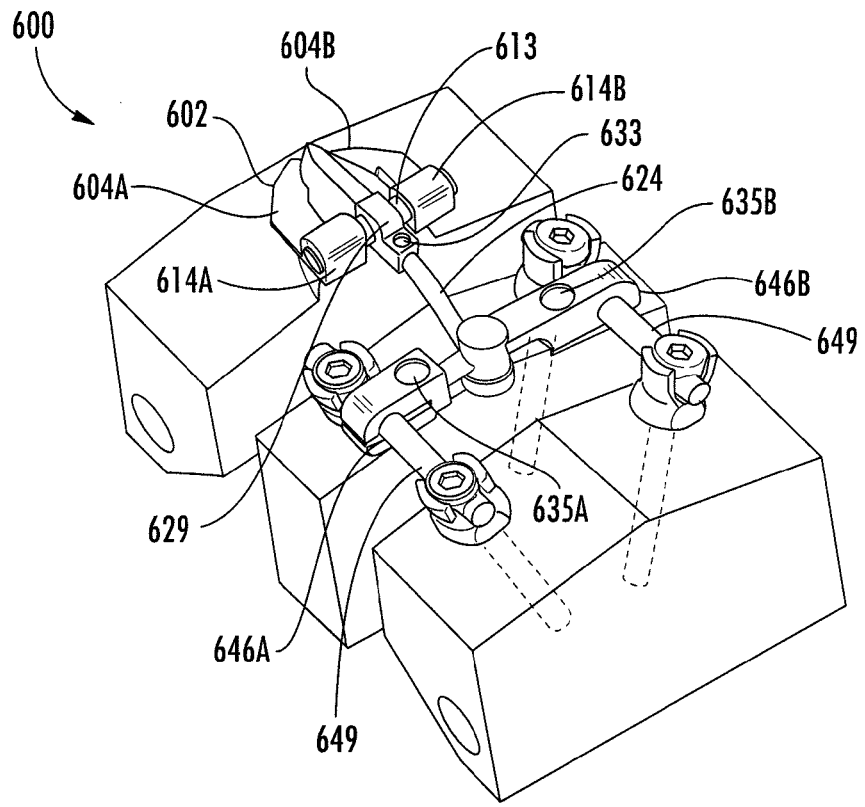
FIG. 29 is a top perspective view of a spinal fixation system including a spinous process clamp, dual pedicle rod clamps forming a stabilizing cross-bar between opposing pedicle screw and rod constructs, and a single rod connecting the spinous process clamp with the cross-bar, according to an embodiment.

FIG. 29 shows a T-style spinous process fixation system 600 having a spinous process clamp 602 having bilateral clamp heads 604 mounted on or formed with curved or bent arms 606. Arms 606 terminate in barrel-like bases 614 which accept therein a mid-bar 613. A mid-bar clamp or acceptor 629 clamps onto or accepts mid-bar 613 (e.g., the mid-bar is threaded through acceptor 629). A single connecting rod 624 extends from clamp/acceptor 629 to join at an opposite end with a stabilization cross-bar 631. Cross-bar 631 includes bilateral pedicle clamps 646 that clamp onto a pedicle rod 649. Clamp 629 and clamps 646 may be tightened via a single screw or pin placed at points 633 and 635, respectively. Connecting rod 624 may connect with cross-bar 631 by a ball-and-socket joint (similar to joints 130 of system 100, but at an opposite end of the connecting rod). Cross-bar 631 may itself be adjustable at a ball-and-socket joint 637, allowing variation of angles between clamp 646A and connecting rod 624 and between clamps 646A and 646B.

Figure 30:
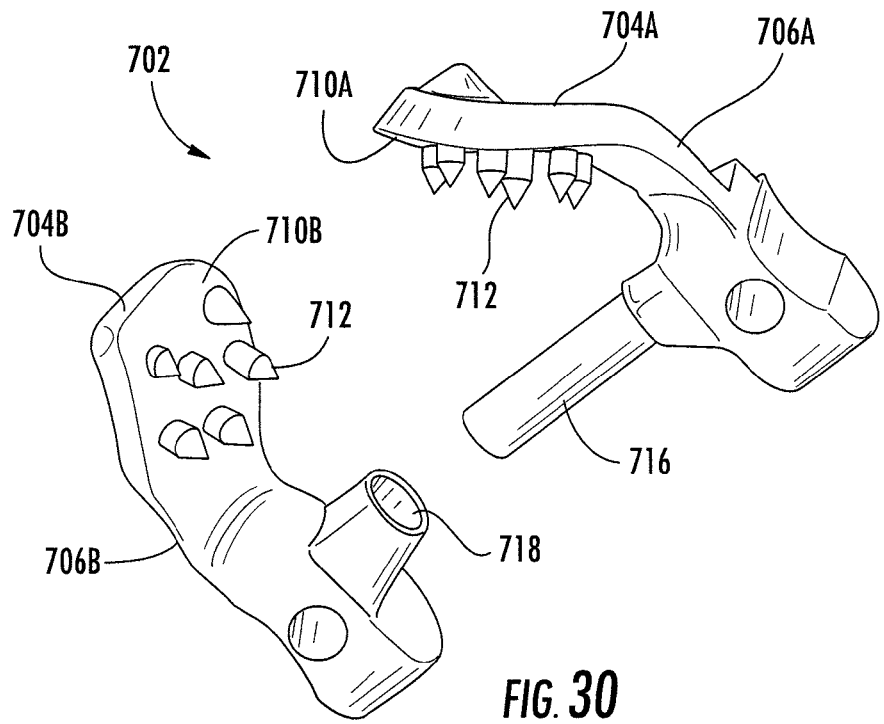
FIG. 30 is a perspective view of a spinous clamp for use with the spinal fixation systems of FIGS. 23-24, 25-26 and 28, 29, according to an embodiment.

FIG. 30 shows an alternate spinous process clamp 702, which may be used with the above-described systems. Clamp 702, shown from the bottom, includes opposing heads 704 extending from opposing bent or curved arms 706. Arm 706B features an internal cylindrical channel 718 for accepting a rod 716 extending from arm 706A. Spikes 712 extending from faces 710 facilitate fixing clamp 702 within spinous process bone. Rod 716 may rotate within channel 718 to allow clamp heads 704 to also rotate with respect to one another, to achieve an optimal fit with a patient's spinal anatomy.

Adjustability of spinous process fixation systems 100-600 and clamp 702 described herein may allow for production of fewer system sizes, as one size may be adjusted to fit a range of spinal sizes and shapes.

The spinal fixation systems/devices disclosed above may achieve stenosis relief (i.e., in patients with prior fusion surgery and Adjacent Level Lumbar Stenosis) while rigidly fixing the superior spinous process. Where inferior adjacent spinous processes are not available, for example due to a laminectomy, the above systems are able to fuse the adjacent level.

Combinations of Features

Features described above as well as those claimed below may be combined in various ways without departing from the scope hereof. The following examples illustrate possible, non-limiting combinations of features of the inventions described above. It should be clear that many changes and modifications may be made to the systems and methods described above without departing from the spirit and scope of this invention:

(a) A spinous process fixation system for attaching with existing pedicle rods includes a spinous clamp having opposing spinous swivel heads mounted with left and right spinous clamp arms, for clamping a spinous process of a patient's spine therebetween. A left socket is proximate the left clamp arm, a right socket proximate the right clamp arm and a barrel base is configured with one of the left and right clamp arms. A shaft configured with the other of the left and right clamp arms is sized to mate with the barrel base to secure the left and right clamp arms together. Left and right connecting rods each have a ball head at an anterior rod end and are configured for fitting with the respective left or right socket via the ball head. A pedicle clamp assembly includes a left clamp body and a right clamp body, each having a medial clamp for clamping the respective left or right connecting rod and a lateral clamp for clamping a left or right pedicle rod of a pre-placed pedicle rod and screw construct. The medial and lateral clamps each include opposing upper and lower swivel heads.

(b) In the system denoted as (a), each of the upper and lower medial and lateral swivel heads of the pedicle clamp assembly may be configured with a pair of opposing wings extending opposite the swivel head, and each of the left and right clamp bodies of the pedicle clamp may comprise an upper plate and a lower plate. Each upper plate may support one upper medial swivel head and one upper lateral swivel head; the swivel heads are mounted within apertures formed through the upper plate and are accessible from atop the upper plate. The opposing wings of the upper medial and lateral swivel heads extend downward from the upper plate apertures. Each lower plate may support one lower medial swivel head and one lower lateral swivel head. The swivel heads may be mounted beneath the lower plate within apertures formed through the lower plate, such that the opposing wing pair of each swivel head extends upwards from the lower plate apertures.

(c) In the system/s denoted as (a) or (b), each swivel head of the pedicle clamp assembly and its opposing wings may form a swivel cup. The upper and lower medial swivel cups may form a cylindrical connecting rod channel therebetween, for accepting the left connecting rod or the right connecting rod, the upper and lower lateral swivel cups may form a cylindrical pedicle rod channel therebetween, for accepting the pedicle rod.

(d) In the system/s denoted as (a)-(c), one of the left and right clamp bodies may include an acceptor for accepting an arm extension of the other of the left and right clamp bodies, the arm extension joining with the acceptor to adjustably link the left and right clamp bodies together.

(e) In the system/s denoted as (a)-(d), an/the arm extension may be raised from an upper surface of the left or right upper plate and curved to increase adjustability of the spinous clamp assembly when the left and right clamp bodies are connected via the arm extension and an/the acceptor.

(f) In the system/s denoted as (e), the acceptor may accept the arm extension within a top slot or a side aperture.

(f) In the system/s denoted as (e) and (f), the acceptor may further include an upper chamber for accepting a fastener above the top slot or side aperture, to secure the arm extension within the top slot or side aperture at a desired position.

(g) In the system/s denoted as (a)-(f), (the) right upper and lower plates of the pedicle clamp assembly may form a right central chamber and (the) left upper and lower plates of the pedicle clamp assembly may form a left central chamber. Each of the left and right central chambers may be shaped to accept a set screw therein, to tighten the upper and lower plates together and lock the upper and lower medial and lateral heads/swivel cups in a desired orientation (h) In the system/s denoted as (g), each of the central chambers may extend vertically through the respective upper and lower plates to facilitate locking the swivel cups in place from above the pedicle clamp assembly.

(i) In the system/s denoted as (b)-(h), for each pair of upper and lower lateral swivel cups, the upper and lower wings on one side of the cylindrical pedicle rod channel may form a tab-and-slot connection, with one of the upper and lower wings forming a tab extension and the other of the upper and lower wings forming a complementary slot sized to accommodate the tab extension, to temporarily attach the upper and lower swivel cups about the pedicle rod.

(j) In the systems denoted as (a)-(i), one or more of the spinous clamp swivel heads, the upper medial pedicle clamp assembly swivel heads and the upper lateral pedicle clamp swivel heads may a dimple socket for accepting an adjustment tool, to facilitate adjustment of swivel head position from atop the spinous process fixation system (k) In the systems denoted as (a)-(j), each spinous clamp swivel head may have a smooth upper face and a lower clamping face for clamping the spinous process, the clamping faces including spikes extending radially therefrom, for penetrating the patient's spinous process to secure the spinous clamp in place about the spinous process.

(l) In the systems denoted as (a)-(k), the left and right spinous clamp arms may form beveled apertures therethrough for supporting the spinous clamp swivel heads such that position of the swivel heads within the apertures may be adjusted.

(m) In the systems denoted as (a)-(l), the left socket and the left ball end and the right socket and the right ball end may form ball and socket joints to facilitate adjustment of width and/or height of left and/or right pedicle clamp bodies relative to the spinous clamp system.

(n) In the systems denoted as (a)-(m), the spinous clamp arms may curve upward and outward from the swivel heads.

(o) In the systems denoted as (a)-(d), height and width of the pedicle clamp assembly relative to the spinous clamp system may be individually adjustable on left and right sides of the spinous process fixation system.

(p) In the systems denoted as (a)-(o), the barrel base may an upper aperture for accepting a set screw to secure the shaft within the barrel base when the left and right halves of the spinous clamp are in a desired orientation.

(p) In the systems denoted as (a)-(o), the barrel base may form a cylindrical space therein and the shaft may be cylindrical shaft sized to fit within the cylindrical space, such that left and right halves of the spinous clamp may rotate with respect to one another.

(q) In the systems denoted as (b)-(p), upper and lower plates of the pedicle clamp assembly may form a plug-and-socket connection therebetween, to orient the upper and lower swivel cups/heads opposite one another when the upper and lower plates are connected via the plug-and-socket connection (r) In the systems denoted as (a)-(q), the left and right connecting rods may terminate in posterior ball ends, to prevent the pedicle clamp assembly from slipping off the connecting rods.

(s) A spinous process fixation system for attaching with existing pedicle rods may include a spinous clamp portion having opposing swivel heads mounted at anterior ends of opposing left and right clamp arms. The left and right clamp arms may extend from posterior left and right bases, and each of the left and right bases may form a ball-and-socket-joint posterior to the left and right clamp arms. A left connecting rod may extend from the left ball-and-socket joint in a direction opposite the left arm and a right connecting rod may extend from the right ball-and-socket joint in a direction opposite the right arm. The left and right bases may join via a cylindrical shaft and channel connection that facilitates fixation of the left and right bases with a customized distance and angle therebetween. A pedicle clamp assembly may connect at an anterior end with the spinous clamp portion via the connecting rods, and with a pre-implanted pedicle clamp and rod assembly at a posterior end. The pedicle clamp assembly may include a left side and a right side, each of the left and right sides comprising a medial connecting rod clamp, for attaching to one of the left and right connecting rods, and a lateral pedicle rod clamp, for clamping to a pedicle rod of the pre-implanted pedicle clamp and rod assembly.

(t) In the system denoted as (s), the connecting rod clamp and pedicle rod clamp may be formed by an upper plate and a lower plate.

(u) In the system denoted as (s) and (t), the upper plate may form medial and lateral beveled apertures for supporting upper medial and lateral swivel cups, and the lower plate may farm opposing medial and lateral apertures for supporting opposing lower medial and lateral swivel cups.

(v) In the systems denoted as (t) and (u), the upper swivel cups may form downward-extending wings and the lower swivel cups may form upward-extending wings.

(w) In the systems denoted as (t)-(v), the medial upper- and lower-extending wings may form a connecting rod channel therebetween for accepting one of the connecting rods, and the lateral upper- and lower-extending wings may form a pedicle rod channel therebetween for accepting a pedicle rod.

(x) In the systems denoted as (t)-(v), the upper plate and the lower plate may be joined by a single set screw between the medial and lateral swivel cups.

(y) In the systems denoted as (s)-(v), the left and right sides of the pedicle clamp assembly may adjustably join together via an arm extension and a complementary acceptor.

(z) A minimally invasive spinous process fixation system that achieves rigid fixation of an adjacent or superior spinous process in case of a laminectomy may include dual rigid metal spinous clamps, each of which may be configured to articulate axially along a cylindrical shaft, and together configured to enclose and clamp inferiorly around the adjacent or superior spinous process by means of opposing and swiveling spherical contact heads with penetrating spikes on spinous contact faces thereof. The spinous clamps are lockable when desired compression is achieved. A pedicle clamp may have right and left clamp bodies for enveloping existing pedicle rods between two consecutive pedicle screws, each of the right and left clamp bodies may include upper and lower rigid metal plates supporting medial and lateral swivel cups with outer swivel heads and inner wings. The opposing upper and lower medial swivel cups may be configured to engage and clamp about a connecting rod extending from the spinous clamp, and the opposing upper and lower lateral swivel heads may be configured to engage and clamp about one of the existing pedicle rods. A channel or aperture may be formed through the upper and lower metal plates, for accepting a locking screw to simultaneously tighten and fix the swivel cups in place about the connecting rod and the pedicle rod. A cross-connection between the right and left clamp bodies may fix the right and left clamp bodies together at a selected position (aa) In the system denoted as (z), at least one of the upper lateral swivel cup wings may form a slot for accepting a tab on the opposite lower lateral swivel cup wing, to temporarily engage the upper and lower swivel cups together about the pedicle rod.

(ab) In the system/s denoted as (z) and (aa), the cross-connection between the right and left clamp bodies may include an open socket formed in a raised portion of an upper surface of one of the right and left upper plates, proximate a medial edge, and a curved shaft extending medially from an upper surface of the other of the right and left upper plates. The shaft is sized to fit within the open socket, and may be secured within the open socket by a set screw.

While the present invention has been described above, it should be clear that many changes and modifications may be made to the process and product without departing from the spirit and scope of this invention. It should also be appreciated that for clarity of illustration, not all features described above are labeled in all drawings.

What is claimed is:

1. A spinous process fixation system for attaching with existing pedicle rods, comprising:
   a spinous clamp having:
   opposing spinous swivel heads mounted within an aperture in a left spinous clamp arm and an aperture in a right spinous clamp arm, for clamping a spinous process of a patient's spine there between, each swivel head configured to move independently of the arm that houses it,
   a left socket proximate the left clamp arm,
   a right socket proximate the right clamp arm, and
   a barrel base configured with one of the left and right clamp arms, and
   a shaft configured with the other of the left and right clamp arms and sized to mate with the barrel base to secure the left and right clamp arms together;
   left and right connecting rods, each having a ball head at an anterior rod end and configured for fitting with the respective left or right socket via the ball head; and
   a pedicle clamp assembly, comprising:
   a left clamp body and a right clamp body, each having a medial clamp for clamping the respective left or right connecting rod and a lateral clamp for clamping a left or right pedicle rod of a pre-placed pedicle rod and screw construct; the medial and lateral clamps each including opposing upper and lower swivel heads; and
   wherein, each of the upper and lower medial and lateral swivel heads of the pedicle clamp assembly configured with a pair of opposing wings extending opposite the swivel head, and each of the left and right clamp bodies of the pedicle clamp comprising an upper plate and a lower plate, wherein:
   each upper plate supports one upper medial swivel head and one upper lateral swivel head, the swivel heads mounted within apertures formed through the upper plate and being accessible from atop the upper plate, the opposing wings of the upper medial and lateral swivel heads extending downward from the upper plate apertures; and
   each lower plate supports one lower medial swivel head and one lower lateral swivel head, the swivel heads being mounted beneath the lower plate within apertures formed through the lower plate, the opposing wing pair of each swivel head extending upwards from the lower plate apertures.

2. The system of claim 1, each swivel head of the pedicle clamp assembly and its opposing wings forming a swivel cup, wherein:
   the upper and lower medial swivel cups form a cylindrical connecting rod channel there between, for accepting the left connecting rod or the right connecting rod, and wherein
   the upper and lower lateral swivel cups form a cylindrical pedicle rod channel there between, for accepting the pedicle rod.

3. The system of claim 2, wherein, for each pair of upper and lower lateral swivel cups, the upper and lower wings on one side of the cylindrical pedicle rod channel form a tab-and-slot connection, one of the upper and lower wings forming a tab extension and the other of the upper and lower wings forming a complementary slot sized to accommodate the tab extension, to temporarily attach the upper and lower swivel cups about the pedicle rod.

4. The fixation system of claim 2, wherein upper and lower plates of the pedicle clamp assembly form a plug-and-socket connection there between, to orient the upper and lower swivel cups opposite one another when the upper and lower plates are connected via the plug-and-socket connection.

5. The system of claim 1, one of the left and right clamp bodies including an acceptor for accepting an arm extension of the other of the left and right clamp bodies, the arm extension joining with the acceptor to adjustably link the left and right clamp bodies together.

6. The system of claim 5, wherein the arm extension is raised from an upper surface of the left or right upper plate and is curved to increase adjustability of the spinous clamp assembly when the left and right clamp bodies are connected via the arm extension and the acceptor.

7. The system of claim 5, the acceptor accepting the arm extension within an a top slot or a side aperture, the acceptor further comprising an upper chamber for accepting a fastener above the top slot or side aperture, to secure the arm extension within the top slot or side aperture at a desired position.

8. The system of claim 1, the right upper and lower plates of the pedicle clamp assembly forming a right central chamber and the left upper and lower plates of the pedicle clamp assembly forming a left central chamber, each of the left and right central chambers shaped to accept a set screw therein, to tighten the upper and lower plates together and lock the upper and lower medial and lateral swivel cups in a desired orientation.

9. The system of claim 8, each of the central chambers extending vertically through the respective upper and lower plates to facilitate locking the swivel cups in place from above the pedicle clamp assembly.

10. The fixation system of claim 1, one or more of the spinous clamp swivel heads, the upper medial pedicle clamp assembly swivel heads and the upper lateral pedicle clamp swivel heads forming a dimple socket for accepting an adjustment tool, to facilitate adjustment of swivel head position from atop the spinous process fixation system.

11. The fixation system of claim 1, each spinous clamp swivel head having a smooth upper face and a lower clamping face for clamping the spinous process, the clamping faces including spikes extending radially therefrom, for penetrating the patient's spinous process to secure the spinous clamp in place about the spinous process.

12. The fixation system of claim 11, the left and right spinous clamp arms forming beveled apertures there through for supporting the spinous clamp swivel heads such that position of the swivel heads within the apertures may be adjusted.

13. The fixation system of claim 1, the left socket and the left ball end and the right socket and the right ball end forming ball and socket joints to facilitate adjustment of width and/or height of left and/or right pedicle clamp bodies relative to the spinous clamp system.

14. The fixation system of claim 1, wherein the spinous clamp arms curve upward and outward from the swivel heads.

15. The fixation system of claim 1, wherein height and width of the pedicle clamp assembly relative to the spinous clamp system is individually adjustable on left and right sides of the spinous process fixation system.

16. The spinous process fixation system of claim 1, the barrel base forming an upper aperture for accepting a set screw to secure the shaft within the barrel base when the left and right halves of the spinous clamp are in a desired orientation.

17. The fixation system of claim 1, wherein the barrel base forms a cylindrical space therein and the shaft is a cylindrical shaft sized to fit within the cylindrical space, such that left and right halves of the spinous clamp may rotate with respect to one another.

18. The fixation system of claim 1, the left and right connecting rods terminating in posterior ball ends, to prevent the pedicle clamp assembly from slipping off the connecting rods.

19. A spinous process fixation system for attaching with existing pedicle rods, comprising:
 a spinous clamp portion having:
 opposing swivel heads mounted at anterior ends of opposing left and right clamp arms, the left and right clamp arms extending from posterior left and right bases, each of the left and right bases forming a ball-and-socket-joint posterior to the left and right clamp arms;
 a left connecting rod extending from the left ball-and-socket joint in a direction opposite the left arm;
 a right connecting rod extending from the right ball-and-socket joint in a direction opposite the right arm,
 wherein the left and right bases join via a cylindrical shaft and channel connection that facilitates fixation of the left and right bases with a customized distance and angle there between; and
 a pedicle clamp assembly for connecting at an anterior end with the spinous clamp portion via the connecting rods, and with pre-implanted pedicle clamp and rod assembly at a posterior end, and comprising:
 a left side and a right side, each of the left and right sides comprising a medial connecting rod clamp, for attaching to one of the left and right connecting rods, and a lateral pedicle rod clamp, for clamping to a pedicle rod of the pre-implanted pedicle clamp and rod assembly.

20. The fixation system of claim 19, the connecting rod clamp and pedicle rod formed by an upper plate and a lower plate, the upper plate forming medial and lateral beveled apertures for supporting upper medial and lateral swivel cups, the lower plate forming opposing medial and lateral apertures for supporting opposing lower medial and lateral swivel cups, the upper swivel cups forming downward-extending wings and the lower swivel cups forming upward-extending wings;
 wherein the medial upper- and lower-extending wings form a connecting rod channel there between for accepting one of the connecting rods;
 wherein the lateral upper- and lower-extending wings form a pedicle rod channel there between for accepting a pedicle rod, and
 wherein the upper plate and the lower plate are joined by a single set screw between the medial and lateral swivel cups, and
 wherein the left and right sides of the pedicle clamp assembly adjustably join together via an arm extension and a complementary acceptor.

21. A minimally invasive spinous process fixation system that achieves rigid fixation of an adjacent or superior spinous process in case of a laminectomy, comprising:
 Dual rigid metal spinous clamps, each configured to articulate axially along a cylindrical shaft, and together configured to enclose and clamp inferiorly around the adjacent or superior spinous process by means of opposing and swiveling spherical contact heads with penetrating spikes on spinous contact faces thereof, the spinous clamps being lockable when desired compression is achieved;

a pedicle clamp comprising right and left clamp bodies for enveloping existing pedicle rods between two consecutive pedicle screws, each of the right and left clamp bodies comprising:

upper and lower rigid metal plates supporting medial and lateral swivel cups with outer swivel heads and inner wings, the opposing upper and lower medial swivel cups configured to engage and clamp about a connecting rod extending from the spinous clamp, and the opposing upper and lower lateral swivel cups configured to engage and clamp about one of the existing pedicle rods;

a channel or aperture through the upper and lower metal plates, for accepting a locking screw to simultaneously tighten and fix the swivel cups in place about the connecting rod and the pedicle rod, and a cross-connection between the right and left clamp bodies for fixing the right and left clamp bodies together at a selected position.

22. The fixation system of claim 21, wherein at least one of the upper lateral swivel cup wings forms a slot for accepting a tab on the opposite lower lateral swivel cup wing, to temporarily engage the upper and lower swivel cups together about the pedicle rod.

23. The fixation system of claim 21, the cross-connection between the right and left clamp bodies comprising:

an open socket formed in a raised portion of an upper surface of one of the right and left upper plates, proximate a medial edge, and a curved shaft extending medially from an upper surface of the other of the right and left upper plates, wherein the shaft is sized to fit within the open socket, and wherein the shaft is secured within the open socket by a set screw.

* * * * *